United States Patent [19]
Vogelstein et al.

[11] Patent Number: 5,693,536
[45] Date of Patent: Dec. 2, 1997

[54] GENE THERAPY WITH MCC

[75] Inventors: Bert Vogelstein; Kenneth W. Kinzler, both of Baltimore, Md.; Raymond White, Salt Lake City, Utah; Yusuke Nakamura, Tokyo, Japan

[73] Assignees: The Johns Hopkins University, Baltimore, Md.; University of Utah, Salt Lake City, Utah; The Cancer Institute, Japan

[21] Appl. No.: 446,549

[22] Filed: May 19, 1995

Related U.S. Application Data

[62] Division of Ser. No. 220,674, Mar. 31, 1994, Pat. No. 5,571,905, which is a division of Ser. No. 670,611, Mar. 13, 1991, Pat. No. 5,330,892.

[51] Int. Cl.$^6$ ........................ C12N 15/63; C12N 15/90; C12N 15/12; A61K 48/00
[52] U.S. Cl. ............... 435/375; 435/69.1; 435/172.3; 435/366; 514/44; 536/23.5
[58] Field of Search ............... 435/172.3, 240.2, 435/375, 366, 69.1; 514/44; 536/23.5; 935/9, 34, 36

[56] References Cited

U.S. PATENT DOCUMENTS 5,330,892  7/1994  Vogelstein et al. ................. 435/6

FOREIGN PATENT DOCUMENTS

A0 284 362  9/1988  European Pat. Off. .
A9 005 180  5/1990  European Pat. Off. .

OTHER PUBLICATIONS

G. Torelli et al. Cancer Research 47 (Oct. 15, 1987) 5266–9.
B. Leggett et al. Gastroenterology 105(5) ('93) 1313–6 (Abstract).
C. Moen et al. PNAS 93 (Feb. '96) 1082–6.
K. Kinzler et al. Science 251 (Mar. 15, 1991) 1366–70.
M. Goyette et al. Mol. Cell Biol. (Mar. 1992) 12(3) 1387–95.
R. Mulligan Science (May 14, 1993) 260: 926–32.
A. Coghlan New Scientist (Nov. 25, 1995) 14–15.
D. Brown, Washington Post, (Dec. 8, 1995) pp. A1 & A22.
K. Culver et al. TIG (1994) 10(5): 174–8.
N. Dillon TIBTECH (May '93) 11: 167–73.
Ashton–Rickardt, et al., "High Frequency of APC Loss in Sporadic Colorectal Carcinoma Due to Breaks Clustered in 5q21–22", Oncogene, 4:1169–1174, (1989).
Bodmer, et al., "Localization of the Gene for Familial Adenomatous Polyposis on Chromosome 5", Nature, 328:614–619, (1987).
Delattre, et al., "Multiple Genetic Alterations in Distal and Proximal Colorectal Cancer," The Lancet, vol. II, No. 8659, pp. 353–356 (Aug. 12, 1989).
Fearon, et al., "Identification of a Chromosome 18q Gene That Is Altered in Colorectal Cancers," Science, 247:49–56 (1990).
Fearon, et al., "A Genetic Model for Colorectal Tumorigenesis," Cell, 61:759–767 (1990).
Herrera, et al., "Brief Clinical Report: Gardner Syndrome in a Man With an Interstitial Deletion of 5q," Am. J. of Med. Genet., 25:473–476 (1986).
Monaco, et al., "Isolation of Candidate cDNAs for Portions of the Duchenne Muscular Dystrophy Gene," Nature, 323:646–650 (1986).
Nakamura, et al., "Localization of the Genetic Defect in Familial Adenomatous Polyposis Within a Small Region of Chromosome 5," Am. J. Hum. Genet., 43:638–644 (1988).
Okayama, et al., "Rapid, Nonradioactive Detection of Mutations in the Human Genome by Allele–Specific Amplification," J. Lab Clin. Med., 114:105–113 (1989).
Rommens, et al., "Identification of the Cystic Fibrosis Gene: Chromosome Walking and Jumping," Science, 245:1059–1065 (1989).
Ruano, et al., "Direct Haplotyping of Chromosomal Segments from Multiple Heterozygotes Via Allele–Specific PCR Amplification," Nucleic Acids Res., 17:8392 (1989).
Sasaki, et al., "Loss of Constitutional Heterozygosity in Colorectal Tumors from Patients with Familial Polyposis Coli and Those with Nonpolyposis Colorectal Carcinoma," Cancer Research, 49:4402–4406, 1989.
Viskochil, et al., "Deletions and a Translocation Interrupt a Cloned Gene at the Neurofibromatosis Type 1 Locus," Cell, 62:187–192 (1990).
Vogelstein, et al., "Genetic Alterations During Colorectal–Tumor Development," New Eng. J. Med., 319:525–532 (1988).
Wallace, et al., "Type 1 Neurofibromatosis Gene: Identification of a Large TRanscript Disrupted in Three NF1 Patients," Science, 249:181–186 (1990).
Wu, et al., "The Ligation Amplification Reaction (LAR)—Amplification of Specific DNA Sequences Using Sequential Rounds of Template–Dependent Ligation," Genomics, 4:560–569, 1989.
International Search Report of Co–pending PCT Application PCT/US92/00377.
Tanaka, et al., "Suppression of Tumorigenicity in Human Colon Carcinoma Cells by Introduction of Normal Chromosome 5 or 18", Nature, 349:340–342 (1991).
Kinzler, et al., "Identification of a Gene Located at Chromosome 5q21 that is Mutated in Colorectal Cancers", Science, 251:1366–1370 (1991).
Marx, "Gene Identified for Inherited Cancer Susceptibility," Science, 253:616 (1991).
Baker et al., "Chromosome 17 Deletions and p53 Gene Mutations in Colorectal Carcinomas", Science, 244:217–221 (1989).

*Primary Examiner*—Charles C. P. Rories
*Attorney, Agent, or Firm*—Banner & Witcoff, Ltd.

[57] ABSTRACT

A new human gene termed MCC is disclosed. Methods and kits are provided for assessing mutations of the MCC gene in human tissues and body samples. Gross rearrangement and point mutations in MCC are observed in human tumor cells. MCC is expressed in most normal tissues. These results suggest that MCC is a tumor suppressor.

3 Claims, 9 Drawing Sheets

FIG. 2A

```
Human cagcacttctgtcctttccctattcccag TGC GAG CAG TCC CAC CTC ATG AGA GAG CAT GAG GAT GTC CAG GAG CGA ACG
Rat       tccgt        cct   gtt  ggc  t              T              A                T    A   C
Human                                  Cys Glu Gln Ser His Leu Met Arg Glu His Glu Asp Val Gln Glu Arg Thr
Rat                                     "   "   "   "   "   "   "   "   "   "   "   "   "   "   "   "   "
                                        ────────────────P1────────────►

Human ACG CTT CGC TAT GAG GAA CGC ATC ACA GAG CTC CAC AGC GTC ATT GCG GAG CTC AAC AAG ATA GAC AAG ATA GAC CGT CTG
Rat    A   C                               G                       A   A                                T   T
Human Thr Leu Arg Tyr Glu Glu Arg Ile Thr Glu Leu His Ser Val Ile Ala Glu Leu Asn Lys Ile Asp Lys Lys Ile Asp Arg Leu
Rat    "   "   "   "   "   "   "   "   "   "   "   "   "   Ile  "   "   "   "   "   "   "   "   "   "   "   "   "
                                                                    ◄────────────────P2────────────────

Human CAA GGC ACC ACC ATC AG gtacgcggctccattcggctttactctgccc
Rat        T                             t gctgctat  aac  g gctgg c tt
Human Gln Gly Thr Thr Ile
Rat    "   "   "   "   "
```

FIG. 2B

```
Human tgttagtggttgccaattcctcctttttctcag G GAG GAA GAT GAG TAC TCA GAA CTG CGA TCA GAA CTC AGC CAG AGC CAA
Rat    cac caat g    agtgctct         tg                             T   G           G            T
Human                                  Glu Glu Asp Glu Tyr Ser Glu Leu Arg Ser Glu Leu Ser Gln Ser Gln
Rat                                                                      "   "   "   "   "   "   "   "
                                                     P3

Human CAC GAG GTC AAC GAG GAC TCT CGA AGC ATG GAC CAA GAC CAG ACC TCT GTC TCT ATC CCC GAA AAC CAG TCT ACC
Rat     A       T   A           C   A   T   G               T   G           G   C           T   G           T
Human His Glu Val Asn Glu Asp Ser Arg Ser Met Asp Gln Asp Gln Thr Ser Val Ser Ile Pro Glu Asn Gln Ser Thr
Rat   Gln  "   "   "   "   "   "   "   "  Val  "   "   "   "   "   "   "   "   "   "   "   "   "   "
                                        P4

Human ATG GTT ACT GCT GAC ATG G gtgagtctgcctgcccttgccaccaagccaga
Rat       C                       t     cagg c c tg tt  ttttct
Human Met Val Thr Ala Asp Met
Rat    "   "   "   "   "   "
```

FIG. 3A

```
  1 CTC CTG CAG CAA TGG CTC GTC CGT GAA ACG CGA GCC ACG GCT GCT CTT TTT

52 AAG AGT GCC TGC ATC CTC CGT TTG CGC TTC GCA ACT GTC CTG GGT GAA AAT

103 GGC TGT CTA GAC TAA AAT GTG GCA GAA GGG ACC AAG CAG TGG ATA TTG AGC

154 CTG TGA AGT CCA ACT CTT AAG CTC CGA GAC CTG GGG GAC TGA GAG CCC AGC

1                 Met Asn Ser Gly Val Ala Met Lys Tyr Gly Asn Asp
205 TCT GAA AAG TGC ATC ATG AAT TCC GGA GTT GCC ATG AAA TAT GGA AAC GAC

13 Ser Ser Ala Glu Leu Ser Glu Leu His Ser Ala Ala Leu Ala Ser Leu Lys
256 TCC TCG GCC GAG CTG AGT GAG CTC CAT TCA GCA GCC CTG GCA TCA CTA AAG

30 Gly Asp Ile Val Glu Leu Asn Lys Arg Leu Gln Gln Thr Glu Arg Glu Arg
307 GGA GAT ATA GTG GAA CTT AAT AAA CGT CTC CAG CAA ACA GAG AGG GAA CGG

47 Asp Leu Leu Glu Lys Lys Leu Ala Lys Ala Gln Cys Glu Gln Ser His Leu
358 GAC CTT CTG GAA AAG AAA TTG GCC AAG GCA CAG TGC GAG CAG TCC CAC CTC

64 Met Arg Glu His Glu Asp Val Gln Glu Arg Thr Thr Leu Arg Tyr Glu Glu
409 ATG AGA GAG CAT GAG GAT GTC CAG GAG CGA ACG ACG CTT CGC TAT GAG GAA

81 Arg Ile Thr Glu Leu His Ser Val Ile Ala Glu Leu Asn Lys Lys Ile Asp
460 CGC ATC ACA GAG CTC CAC AGC GTC ATT GCG GAG CTC AAC AAG AAG ATA GAC

98 Arg Leu Gln Gly Thr Thr Ile Arg Glu Glu Asp Glu Tyr Ser Glu Leu Arg
511 CGT CTG CAA GGC ACC ACC ATC AGG GAG GAA GAT GAG TAC TCA GAA CTG CGA

115 Ser Glu Leu Ser Gln Ser Gln His Glu Val Asn Glu Asp Ser Arg Ser Met
562 TCA GAA CTC AGC CAG AGC CAA CAC GAG GTC AAC GAG GAC TCT CGA AGC ATG

132 Asp Gln Asp Gln Thr Ser Val Ser Ile Pro Glu Asn Gln Ser Thr Met Val
613 GAC CAA GAC CAG ACC TCT GTC TCT ATC CCC GAA AAC CAG TCT ACC ATG GTT

149 Thr Ala Asp Met Asp Asn Cys Ser Asp Leu Asn Ser Glu Leu Gln Arg Val
664 ACT GCT GAC ATG GAC AAC TGC AGT GAC CTG AAC TCA GAA CTG CAG AGG GTG

166 Leu Thr Gly Leu Glu Asn Val Val Cys Gly Arg Lys Lys Ser Ser Cys Ser
715 CTG ACA GGG CTG GAG AAT GTT GTC TGC GGC AGG AAG AAG AGC AGC TGC AGC

183 Leu Ser Val Ala Glu Val Asp Arg His Ile Glu Gln Leu Thr Thr Ala Ser
766 CTC TCC GTG GCC GAG GTG GAC AGG CAC ATT GAG CAG CTC ACC ACA GCC AGC

200 Glu His Cys Asp Leu Ala Ile Lys Thr Val Glu Glu Ile Glu Gly Val Leu
817 GAG CAC TGT GAC CTG GCT ATT AAG ACA GTC GAG GAG ATT GAG GGG GTG CTT

217 Gly Arg Asp Leu Tyr Pro Asn Leu Ala Glu Glu Arg Ser Arg Trp Glu Lys
868 GGC CGG GAC CTG TAT CCC AAC CTG GCT GAA GAG AGG TCT CGG TGG GAG AAG

234 Glu Leu Ala Gly Leu Arg Glu Glu Asn Glu Ser Leu Thr Ala Met Leu Cys
919 GAG CTG GCT GGG CTG AGG GAA GAG AAT GAG AGC CTG ACT GCC ATG CTG TGC
```

FIG. 3B

```
 251  Ser Lys Glu Glu Glu Leu Asn Arg Thr Lys Ala Thr Met Asn Ala Ile Arg
 970  AGC AAA GAG GAA GAA CTG AAC CGG ACT AAG GCC ACC ATG AAT GCC ATC CGG

268  Glu Glu Arg Asp Arg Leu Arg Arg Arg Val Arg Glu Leu Gln Thr Arg Leu
1021  GAA GAG CGG GAC CGG CTC CGG AGG CGG GTC AGA GAG CTT CAA ACT CGA CTA

285  Gln Ser Val Gln Ala Thr Gly Pro Ser Ser Pro Gly Arg Leu Thr Ser Thr
1072  CAG AGC GTG CAG GCC ACA GGT CCC TCC AGC CCT GGC CGC CTC ACT TCC ACC

302  Asn Arg Pro Ile Asn Pro Ser Thr Gly Glu Leu Ser Thr Ser Ser Ser Ser
1123  AAC CGC CCG ATT AAC CCC AGC ACT GGG GAG CTG AGC ACA AGC AGC AGC AGC

319  Asn Asp Ile Pro Ile Ala Lys Ile Ala Glu Arg Val Lys Leu Ser Lys Thr
1174  AAT GAC ATT CCC ATC GCC AAG ATT GCT GAG AGG GTG AAG CTA TCA AAG ACA

336  Arg Ser Glu Ser Ser Ser Ser Asp Arg Pro Val Leu Gly Ser Glu Ile Ser
1225  AGG TCC GAA TCG TCA TCA TCT GAT CGG CCA GTC CTG GGC TCA GAA ATC AGT

353  Ser Ile Gly Val Ser Ser Ser Val Ala Glu His Leu Ala His Ser Leu Gln
1276  AGC ATA GGG GTA TCC AGC AGT GTG GCT GAA CAC CTG GCC CAC TCA CTT CAG

370  Asp Cys Ser Asn Ile Gln Glu Ile Phe Gln Thr Leu Tyr Ser His Gly Ser
1327  GAC TGC TCC AAT ATC CAA GAG ATT TTC CAA ACA CTC TAC TCA CAC GGA TCT

387  Ala Ile Ser Glu Ser Lys Ile Arg Glu Phe Glu Val Glu Thr Glu Arg Leu
1378  GCC ATC TCA GAA AGC AAG ATT AGA GAG TTT GAG GTG GAA ACA GAA CGG CTG

404  Asn Ser Arg Ile Glu His Leu Lys Ser Gln Asn Asp Leu Leu Thr Ile Thr
1429  AAT AGC CGG ATT GAG CAC CTC AAA TCC CAA AAT GAC CTC CTG ACC ATA ACC

421  Leu Glu Glu Cys Lys Ser Asn Ala Glu Arg Met Ser Met Leu Val Gly Lys
1480  TTG GAG GAA TGT AAA AGC AAT GCT GAG AGG ATG AGC ATG CTG GTG GGA AAA

438  Tyr Glu Ser Asn Ala Thr Ala Leu Arg Leu Ala Leu Gln Tyr Ser Glu Gln
1531  TAC GAA TCC AAT GCC ACA GCG CTG AGG CTG GCC TTG CAG TAC AGC GAG CAG

455  Cys Ile Glu Ala Tyr Glu Leu Leu Leu Ala Leu Ala Glu Ser Glu Gln Ser
1582  TGC ATC GAA GCC TAC GAA CTC CTC CTG GCG CTG GCA GAG AGT GAG CAG AGC

472  Leu Ile Leu Gly Gln Phe Arg Ala Ala Gly Val Gly Ser Ser Pro Gly Asp
1633  CTC ATC CTG GGG CAG TTC CGA GCG GCG GGC GTG GGG TCC TCC CCT GGA GAC

489  Gln Ser Gly Asp Glu Asn Ile Thr Gln Met Leu Lys Arg Ala His Asp Cys
1684  CAG TCG GGG GAT GAA AAC ATC ACT CAG ATG CTC AAG CGA GCT CAT GAC TGC

506  Arg Lys Thr Ala Glu Asn Ala Ala Lys Ala Leu Leu Met Lys Leu Asp Gly
1735  CGG AAG ACA GCT GAG AAC GCT GCC AAG GCC CTG CTC ATG AAG CTG GAC GGC

523  Ser Cys Gly Gly Ala Phe Ala Val Ala Gly Cys Ser Val Gln Pro Trp Glu
1786  AGC TGT GGG GGA GCC TTT GCC GTG GCC GGC TGC AGC GTG CAG CCC TGG GAG

540  Ser Leu Ser Ser Asn Ser His Thr Ser Thr Thr Ser Ser Thr Ala Ser Ser
1837  AGC CTT TCC TCC AAC AGC CAC ACC AGC ACA ACC AGC TCC ACA GCC AGT AGT
```

FIG. 3C

```
557  Cys Asp Thr Glu Phe Thr Lys Glu Asp Glu Gln Arg Leu Lys Asp Tyr Ile
1888 TGC GAC ACC GAG TTC ACT AAA GAA GAC GAG CAG AGG CTG AAG GAT TAT ATC

574  Gln Gln Leu Lys Asn Asp Arg Ala Ala Val Lys Leu Thr Met Leu Glu Leu
1939 CAG CAG CTC AAG AAT GAC AGG GCT GCG GTC AAG CTG ACC ATG CTG GAG CTG

591  Glu Ser Ile His Ile Asp Pro Leu Ser Tyr Asp Val Lys Pro Arg Gly Asp
1990 GAA AGC ATC CAC ATC GAT CCT CTC AGC TAT GAC GTC AAG CCT CGG GGA GAC

608  Ser Gln Arg Leu Asp Leu Glu Asn Ala Val Leu Met Gln Glu Leu Met Ala
2041 AGC CAG AGG CTG GAT CTG GAA AAC GCA GTG CTT ATG CAG GAG CTC ATG GCC

625  Met Lys Glu Glu Met Ala Glu Leu Lys Ala Gln Leu Tyr Leu Leu Glu Lys
2092 ATG AAG GAG GAG ATG GCC GAG TTG AAG GCC CAG CTC TAC CTA CTG GAG AAA

642  Glu Lys Lys Ala Leu Glu Leu Lys Leu Ser Thr Arg Glu Ala Gln Glu Gln
2143 GAG AAG AAG GCC CTG GAG CTG AAG CTG AGC ACG CGG GAG GCC CAG GAG CAG

659  Ala Tyr Leu Val His Ile Glu His Leu Lys Ser Glu Val Glu Glu Gln Lys
2194 GCC TAC CTG GTG CAC ATT GAG CAC CTG AAG TCC GAG GTG GAG GAG CAG AAG

676  Glu Gln Arg Met Arg Ser Leu Ser Ser Thr Ser Ser Gly Ser Lys Asp Lys
2245 GAG CAG CGG ATG CGA TCC CTC AGC TCC ACC AGC AGC GGC AGC AAA GAT AAA

693  Pro Gly Lys Glu Cys Ala Asp Ala Ala Ser Pro Ala Leu Ser Leu Ala Glu
2296 CCT GGC AAG GAG TGT GCT GAT GCT GCC TCC CCA GCT CTG TCC CTA GCT GAA

710  Leu Arg Thr Thr Cys Ser Glu Asn Glu Leu Ala Ala Glu Phe Thr Asn Ala
2347 CTC AGG ACA ACG TGC AGC GAG AAT GAG CTG GCT GCG GAG TTC ACC AAC GCC

727  Ile Arg Arg Glu Lys Lys Leu Lys Ala Arg Val Gln Glu Leu Val Ser Ala
2398 ATT CGT CGA GAA AAG AAG TTG AAG GCC AGA GTT CAA GAG CTG GTG AGT GCC

744  Leu Glu Arg Leu Thr Lys Ser Ser Glu Ile Arg His Gln Gln Ser Ala Glu
2449 TTG GAG AGA CTC ACC AAG AGC AGT GAA ATC CGA CAT CAG CAA TCT GCA GAG

761  Phe Val Asn Asp Leu Lys Arg Ala Asn Ser Asn Leu Val Ala Ala Tyr Glu
2500 TTC GTG AAT GAT CTA AAG CGG GCC AAC AGC AAC CTG GTG GCT GCC TAT GAG

778  Lys Ala Lys Lys Lys His Gln Asn Lys Leu Lys Lys Leu Glu Ser Gln Met
2551 AAA GCA AAG AAA AAG CAT CAA AAC AAA CTG AAG AAG TTA GAG TCG CAG ATG

795  Met Ala Met Val Glu Arg His Glu Thr Gln Val Arg Met Leu Lys Gln Arg
2602 ATG GCC ATG GTG GAG AGA CAT GAG ACC CAA GTG AGG ATG CTC AAG CAA AGA

812  Ile Ala Leu Leu Glu Glu Glu Asn Ser Arg Pro His Thr Asn Glu Thr Ser
2653 ATA GCT CTG CTA GAG GAG GAG AAC TCC AGG CCA CAC ACC AAT GAA ACT TCG

829  Leu
2704 CTT TAA TCA GCA CTC ACG CAC CGG AGT TCT GCC CAT GGG AAG TAA ACT GCA

2755 GCA GGC CAC TGG GGA CAG AAG GGC CCA TGT ACT TGT TGG GAG GAG GAG GAA
```

FIG. 3D

```
2806  AGG GAA GGC TGG CAG GTA GGT CGG CAC TTG GAC AAT GGA GTG CCC CAA CTC
2857  AAC CCT TGG GGT GAC TGG CCA TGG TGA CAT TGT GGA CTG TAT CCA GAG GTG
2908  CCC GCT CTT CCC TCC TGG GCC CAC AAC AGC GTG TAA ACA CAT GTT CTG TGC
2959  CTG CTC AGC AGA GCC TCG TTT CTG CTT TCA GCA CTC ACT CTC CCC CTC CTC
3010  TTC TGG TCT GGC GGC TGT GCA TCA GTG GGA TCC CAG ACA TTT GTT TCT GTA
3061  AGA TTT TCC ATT GTA TCC TCT TTT TGG TAG ATG CTG GGC TCA TCT TCT AGA
3112  ATC TCG TTT CTC CTC TTT CCT CCT GCT TCA TGG GAA AAC AGA CCT GTG TGT
3163  GCC TCC AGC ATT TAA AAG GAC TGC TGA TTT GTT TAC TAC AGC AAG GCT TTG
3214  GTT TCC AAG TCC CGG GTC TCA ACT TTA AGA TAG AGG CGG CCA TAA GAG GTG
3265  ATC TCT GGG AGT TAT AGG TCA TGG GAA GAG CGT AGA CAG GTG TTA CTT ACA
3316  GTC CCA GAT ACA CTA AAG TTA CAA ACA GAC CAC CAC CAG GAC TGT GCC TGA
3367  ACA ATT TTG TAT TGA GAG AAT AAA AAC TTC CTT CAA TCT TCA TTT TGG AGG
3418  CAG GGC TGG GAA GGG AGC GCT CTC TTG ATT CTG GGA TTT CTC CCT CTC AGT
3469  GGA GCC TTA TTA ATA TCC AAG ACT TAG AGC TGG GAA TCT TTT TGA TAC CTG
3520  TAG TGG AAC TAA AAT TCT GTC AGG GGT TTC TTC AAG AGC TGA GAA ACA TTA
3571  TTA GCA CTT CCC GCC CCA GGG CAC TAC ATA ATT GCT GTT CTG CTG AAT CAA
3622  ATC TCT TCC ACA TGG GTG CAT TTG TAG CTC TGG ACC TGT CTC TAC CTA AGG
3673  ACA AGA CAC TGA GGA GAT ACT GAA CAT TTT GCA AAA CTT ATC ACG CCT ACT
3724  TAA GAG TGC TGT GTA ACC CCC AGT TCA AGA CTT AGC TCC TGT TGT CAT GAC
3775  GGG GAC AGA GTG AGG GAA TGG TAG TTA AGG CTT CTT TTT TGC CCC CAG ATA
3826  CAT GGT GAT GGT TAG CAT ATG GTG CTT AAA AGG TTA AAT TTC AAG CAA AAT
3877  GCT TAC AGG GCT AGG CAG TAC CAA AGT AAC TGA ATT ATT TCA GGA AGG TCT
3928  TCA ATC TTA AAA CAA ATT CAT TAT TCT TTT TCA GTT TTA CCT CTT CTC TCT
3979  CAG TTC TAC ACT GAT ACA CTT GAA GGA CCA TTT ACT GTT TTT TTC TGT AGC
4030  ACC AGA GAA TCC ATC CAA AGT TCC CTA TGA AAA ATG TGT TCC ATT GCC ATA
4081  GCT GAC TAC AAA TTA AAG TTG AGG AGG TTT CTG CAT AGA GTC TTT ATG TCC
4132  ATA AGC TAC GGG TAG GTC TAT TTT CAG AGC ATG ATA CAA ATT CCA CAG G
```

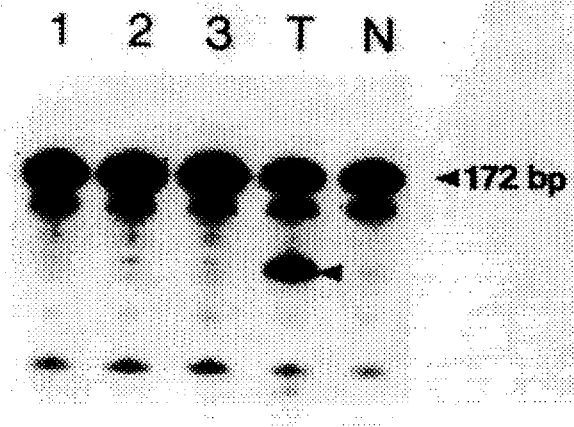
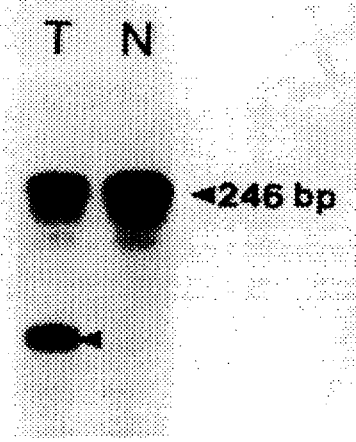

FIG. 5

```
MCC        220  LYPNLAEERSRWEKELAGLREENE  243
                ||  :  |  :  ||||||
M3 mAChR   249  LYWRIYKETEKRTKELAGLQASGT  272

DOMAIN A              YKETEKRTKE

DOMAIN B                        LAGLQASGT
```

GENE THERAPY WITH MCC

This application is a division of application Ser. No. 08/220,674, filed Mar. 31, 1994, now U.S. Pat. No. 5,571,905 issued Nov. 5, 1996, which is a division of Ser. No. 07/670,611 filed Mar. 13, 1991 now U.S. Pat. No. 5,330,892 issued Jul. 19, 1994.

The U.S. Government has a paid-up license in this invention and the right in limited circumstances to require the patent owner to license others on reasonable terms as provided for by the terms of grants awarded by the National Institutes of Health.

TECHNICAL AREA OF THE INVENTION

The invention relates to the area of cancer diagnostics and therapeutics. More particularly, the invention relates to detection of the alteration of wild-type MCC genes in tumor tissues. In addition, it relates to therapeutic intervention to restore the function of MCC gene product.

BACKGROUND OF THE INVENTION

According to the model of Knudson for tumorigenesis (Cancer Research, vol. 45, p. 1482, 1985), there are tumor suppressor genes in all normal cells which, when they become non-functional due to mutation, cause neoplastic development. Evidence for this model has been found in the cases of retinoblastoma and colorectal tumors. The implicated suppressor genes in those tumors, RB and p53 and DCC, were found to be deleted or altered in many cases of the tumors studied. (Hansen and Cavenee, Cancer Research, vol. 47, pp. 5518–5527 (1987); Baker et al., Science, vol. 244, p. 217 (1989); Fearon et al., Science, vol. 247, p. 49 (1990).)

In order to fully understand the pathogenesis of tumors, it will be necessary to identify the other suppressor genes that play a role in the tumorigenesis process. Prominent among these is the one(s) presumptively located at 5q21. Cytogenetic (Herrera et al., Am J. Med. Genet, vol. 25, pg. 473 (1986) and linkage (Leppert et al., Science, vol. 238, pg. 1411 (1987); Bodmer et al., Nature, vol. 328, pg. 614 (1987)) studies have shown that this chromosome region harbors the gene responsible for familial adenomatous polyposis (FAP), an autosomal-dominant, inherited disease in which affected individuals develop hundreds to thousands of adenomatous polyps, some of which progress to malignancy. Additionally, this chromosomal region is often deleted from the adenomas (Vogelstein et al., N. Engl. J. Med., vol. 319, pg. 525 (1988)) and carcinomas (Vogelstein et al., N. Engl. J. Med., vol. 319, pg. 525 (1988); Solomon et al., Nature, vol. 328, pg. 616 (1987); Sasaki et al., Cancer Research, vol. 49, pg. 4402 (1989); Delattre et al., Lancet, vol. 2, pg. 353 (1989); and Ashton-Rickardt et al., Oncogene, vol. 4, pg. 1169 (1989)) of patients without FAP. Thus, a putative suppressor gene on chromosome 5q21 appears to play a role in the early stages of colorectal neoplasia in both sporadic and familial tumors. However, no gene has been identified on 5q21 which is a candidate suppressor gene. Thus there is a need in the art for investigations of this chromosomal region to identify genes and to determine if any of such genes are associated with the process of tumorigenesis.

SUMMARY OF THE INVENTION

It is an object of the present invention to provide a method for diagnosing and prognosing a neoplastic tissue of a human.

It is another object of the invention to provide a method of supplying wild-type MCC gene function to a cell which has lost said gene function.

It is yet another object of the invention to provide a kit for determination of the nucleotide sequence of MCC alleles by the polymerase chain reaction.

It is still another object of the invention to provide nucleic acid probes for detection of mutations in the human MCC gene.

It is another object of the invention to provide a method of detecting genetic predisposition to cancer.

It is still another object of the invention to provide a cDNA molecule encoding the MCC gene product.

It is yet another object of the invention to provide a preparation of the human MCC protein.

These and other objects of the invention are provided by one or more of the embodiments which are described below. In one embodiment of the present invention a method of diagnosing or prognosing a neoplastic tissue of a human is provided comprising: isolating a tissue from a human; and detecting alteration of wild-type MCC genes or their expression products from said tissue, said alteration indicating neoplasia of the tissue.

In another embodiment of the present invention a method is provided for supplying wild-type MCC gene function to a cell which has lost said gene function by virtue of a mutation in the MCC gene, comprising: introducing a wild-type MCC gene into a cell which has lost said gene function such that said wild-type gene is expressed in the cell.

In another embodiment a method of supplying wild-type MCC gene function to a cell is provided comprising introducing a portion of a wild-type MCC gene into a cell which has lost said gene function such that said portion is expressed in the cell, said portion encoding a part of the MCC protein which is required for non-neoplastic growth of said cell. Synthetic peptides or drugs can also be used to mimic MCC function in cells which have altered MCC expression.

In yet another embodiment a pair of single stranded primers is provided for determination of the nucleotide sequence of the MCC gene by polymerase chain reaction. The sequence of said pair of single stranded DNA primers is derived from chromosome 5q band 21, said pair of primers allowing synthesis of MCC gene coding sequences.

In still another embodiment of the invention a nucleic acid probe is provided which is complementary to human wild-type MCC gene coding sequences and which can form mismatches with mutant MCC genes, thereby allowing their detection by enzymatic or chemical cleavage or by shifts in electrophoretic mobility.

In another embodiment of the invention a method is provided for detecting the presence of a neoplastic tissue in a human. The method comprises isolating a body sample from a human; detecting in said sample alteration of a wild-type MCC gene sequence or wild-type MCC expression product, said alteration indicating the presence of a neoplastic tissue in the human.

In yet another embodiment a method is provided of detecting genetic predisposition to cancer in a human, comprising: isolating a human sample selected from the group consisting of blood and fetal tissue; detecting alteration of wild-type MCC gene coding sequences or their expression products from the sample, said alteration indicating genetic predisposition to cancer.

In still another embodiment a cDNA molecule is provided which comprises the coding sequence of the MCC gene.

In even another embodiment a preparation of the human MCC protein is provided which is substantially free of other human proteins. The amino acid sequence of the protein is shown in SEQ ID NO: 2.

The present invention provides the art with the information that the MCC gene, a heretofore unknown gene is, in fact, a target of mutational alterations on chromosome 5q21 and that these alterations are associated with the process of tumorigenesis. This information allows highly specific assays to be performed to assess the neoplastic status of a particular tissue or the predisposition to cancer of an individual.

BRIEF DESCRIPTION OF THE DRAWINGS

FIG. 2 (A and B) shows the sequence of putative exons from the 5.71 cosmid. Panel A shows the sequence of the 5.71-5 exon and the related rat exon. Panel B shows the sequence of the 5.71-3 exon and the related rat exon. Rat sequences are listed only where they differ from the human sequence. Lower case letters signify introns surrounding the exons. The primers used for PCR are demarcated by arrows. Primers P2 and P4 were reversed and complemented relative to the sequence shown.

FIG. 3 shows the nucleotide sequence of the MCC cDNA and predicted amino acid sequence. The sequence shown represents the composite sequence of seven overlapping clones.

FIG. 4 (A and B) shows PCR—RNase Protection Analysis. The analysis was performed on PCR products and the resulting cleavage products separated by denaturing gel electrophoresis. Panel A shows the results of analysis of the exon encoding nucleotides 2305 to 2405. Lanes 1, 2, and 3 show the results obtained from DNA isolated from three different tumors that did not show any changes. Lanes marked T and N show the results obtained from DNA isolated from patient 91's tumor or normal cells, respectively. Panel B show the results of analysis of the exon encoding nucleotides 1679–1862. Lanes marked T and N show the results obtained from DNA isolated from patient 35's tumor and normal cells, respectively.

FIG. 5 shows a comparison of MCC and the G Protein activating region of human m3 muscarinic acetylcholine receptor (mAChR). Connecting lines indicate identities; dots indicate related amino acid residues. Domain A refers to the 10 amino acid region which, when deleted, alters G protein responses. Domain B refers to the 9 amino acids which can mediate specificity of mAChR G protein coupling.

DETAILED DESCRIPTION

Figure 1A:
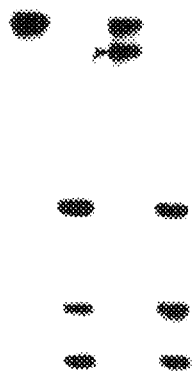
FIG. 1 (A–C) shows a Southern blot analysis of tumor T14 demonstrating a somatic change. Lanes 1 and 2 contain 5 ug of DNA isolated from normal tissue of patient T14; Lanes 3 and 4 contain 5 ug of DNA isolated from the T14 colon carcinoma. Lanes 1 and 3 were cleaved with Eco RI; Lanes 2 and 4 were cleaved with Pst I. The Southern blot in panel A was hybridized to a subclone of cosmid 5.71 (5.71-3). Panels B (3 hour exposure) and C (20 hour exposure) show the same Southern blot hybridized with the abnormal 11 kb fragment cloned from the T14 tumor. The daggers indicate the novel alterations in T14. The size markers indicated on the right represent HindIII-cleaved lambda phage DNA and HaeIII-cleaved PhiX phage DNA.

It is a discovery of the present invention that mutational events associated with tumorigenesis occur in a previously unknown gene on chromosome 5q named here the MCC (Mutated in Colorectal Cancer) gene. Although it was previously known that deletion of alleles on chromosome 5q were common in certain types of cancers, it was not known that a target gene of these deletions was the MCC gene. Further it was not known that other types of mutational events in the MCC gene are also associated with cancers. The mutations of the MCC gene can involve gross rearrangements, such as insertions and deletions. Point mutations have also been observed.

According to the diagnostic and prognostic method of the present invention, alteration of the wild-type gene Is detected. "Alteration of a wild-type gene" according to the present invention encompasses all forms of mutations—including deletions. The alteration may be due to either rearrangements such as insertions, inversions, and deletions, or to point mutations. Deletions may by of the entire gene or only a portion of the gene. If only a single allele is mutated, an early neoplastic state is indicated. However, if both alleles are mutated then a late neoplastic state is indicated. The finding of MCC mutations thus provides both diagnostic and prognostic information. An MCC allele which is not deleted (e.g., that on the sister chromosome to a chromosome carrying an MCC deletion) can be screened for other mutations, such as insertions, small deletions, and point mutations. It is believed that many mutations found in tumor tissues will be those leading to decreased expression of the MCC gene product. However, mutations leading to non-functional gene products would also lead to a cancerous state. Point mutational events may occur in regulatory regions, such as in the promoter of the gene, leading to loss or diminution of expression of the mRNA. Point mutations may also abolish proper RNA processing, leading to loss of expression of the MCC gene product.

In order to detect the alteration of the wild-type MCC gene in a tissue, it is helpful to isolate the tissue free from surrounding normal tissues. Means for enriching a tissue preparation for tumor cells are known in the art. For example, the tissue may be isolated from paraffin or cryostat sections. Cancer cells may also be separated from normal cells by flow cytometry. These as well as other techniques for separating tumor from normal cells are well known in the art. If the tumor tissue is highly contaminated with normal cells, detection of mutations is more difficult.

Detection of point mutations may be accomplished by molecular cloning of the allele (or alleles) present in the tumor tissue and sequencing that allele(s) using techniques well known in the art. Alternatively, the polymerase chain reaction (PCR) can be used to amplify gene sequences directly from a genomic DNA preparation from the tumor tissue. The DNA sequence of the amplified sequences can then be determined. The polymerase chain reaction itself is well known in the art. See, e.g., Saiki et al., Science, Vol. 239, p. 487, 1988; U.S. Pat. Nos. 4,683,203; and 4,683,195. Specific primers which can be used in order to amplify the gene will be discussed in more detail below. The ligase chain reaction, which is known in the art, can also be used to amplify MCC sequences. See Wu et al., (Genomics, vol. 4, pp. 560–569 (1989). In addition, a technique known as allele specific PCR can be used. (See Ruano and Kidd, Nucleic Acids Research, vol 17, p. 8392, 1989.) According to this technique, primers are used which hybridize at their 3' ends to a particular MCC mutation. If the particular MCC mutation is not present, an amplification product is not observed. Insertions and deletions of genes can also be detected by cloning, sequencing and amplification. In addition, restriction fragment length polymorphism (RFLP) probes for the gene or surrounding marker genes can be used to score alteration of an allele or an insertion in a polymorphic fragment. Other techniques for detecting insertions and deletions as are known in the art can be used.

Alteration of wild-type genes can also be detected on the basis of the alteration of a wild-type expression product of the gene. Such expression products include both the mRNA as well as the protein product itself. The sequences of these products are shown in SEQ ID NOS: 1 and 2. Point mutations may be detected by amplifying and sequencing the mRNA or via molecular cloning of cDNA made from the mRNA. The sequence of the cloned cDNA can be determined using DNA sequencing techniques which are well known in the art. The cDNA can also be sequenced via the polymerase chain reaction (PCR) which will be discussed in more detail below.

Mismatches, according to the present invention are hybridized nucleic acid duplexes which are not 100% homologous. The lack of total homology may be due to deletions, insertions, inversions, substitutions or frameshift mutations. Mismatch detection can be used to detect point mutations in the gene or its mRNA product. While these techniques are less sensitive than sequencing, they are simpler to perform on a large number of tumor samples. An example of a mismatch cleavage technique is the RNase protection method, which is described in detail in Winter et al., Proc. Natl. Acad. Sol. USA, Vol. 82, p. 7575, 1985 and Meyers et al., Science, Vol. 230, p. 1242, 1985. In the practice of the present invention the method involves the use of a labeled riboprobe which is complementary to the human wild-type gene ceding sequence. The riboprobe and either mRNA or DNA isolated from the tumor tissue are annealed (hybridized) together and subsequently digested with the enzyme RNase A which is able to detect some mismatches in a duplex RNA structure. If a mismatch is detected by RNase A, it cleaves at the site of the mismatch. Thus, when the annealed RNA preparation is separated on an electrophoretic gel matrix, if a mismatch has been detected and cleaved by RNase A, an RNA product will be seen which is smaller than the full-length duplex RNA for the riboprobe and the mRNA or DNA. The riboprobe need not be the full length of the MCC mRNA or gene but can be a segment of either. If the riboprobe comprises only a segment of the MCC mRNA or gene it will be desirable to use a number of these probes to screen the whole mRNA sequence for mismatches.

In similar fashion, DNA probes can be used to detect mismatches, through enzymatic or chemical cleavage. See, e.g., Cotton et al., Proc. Natl. Acad. Sci. USA, vol. 85, 4397, 1988; and Shenk et al., Proc. Natl. Aced. Sci. USA, vol. 72, p. 989, 1975. Alternatively, mismatches can be detected by shifts in the electrophoretic mobility of mismatched duplexes relative to matched duplexes. See, e.g., Cariello, Human Genetics, vol. 42, p. 726, 1988. With either riboprobes or DNA probes, the cellular mRNA or DNA which might contain a mutation can be amplified using PCR (see below) before hybridization. Changes in DNA of the MCC gene can also be detected using Southern hybridization, especially if the changes are gross rearrangements, such as deletions and insertions.

DNA sequences of the MCC gene from the tumor tissue which have been amplified by use of polymerase chain reaction may also be screened using allele-specific probes. These probes are nucleic acid oligomers, each of which contains a region of the MCC gene sequence harboring a known mutation. For example, one oligomer may be about 30 nucleotides in length, corresponding to a portion of the MCC gene sequence. By use of a battery of such allele-specific probes, PCR amplification products can be screened to identify the presence of a previously identified mutation in the MCC gene. Hybridization of allele-specific probes with amplified MCC sequences can be performed, for example, on a nylon filter. Hybridization to a particular probe under stringent hybridization conditions indicates the presence of the same mutation In the tumor tissue as in the allele-specific probe.

Alteration of MCC mRNA expression can be detected by any technique known in the art. These include Northern blot analysis, PCR amplification and RNase protection, Diminished mRNA expression indicates an alteration of the wild-type MCC gene.

Alteration of wild-type MCC genes can also be detected by screening for alteration of wild-type MCC protein, For example, monoclonal antibodies immunoreactive with MCC can be used to screen a tissue. Lack of cognate antigen would indicate an MCC mutation. Antibodies specific for products of mutant alleles could also be used to detect mutant MCC gene product. Such immunological assays could be done in any convenient format known in the art. These include Western blots, immunohistochemical assays and ELISA assays. Any means for detecting an altered MCC protein can be used to detect alteration of wild-type MCC genes, Functional assays can be used, such as protein binding determinations. For example, it is believed that MCC protein binds to a G protein. Thus, an assay for the binding partner to that G protein can be employed. In addition, assays can be used which detect MCC biochemical function. It is believed that MCC is involved in phospholipid metabolism. Thus, assaying the enzymatic products of the involved phospholipid metabolic pathway can be used to determine MCC activity. Finding a mutant MCC gene product indicates alteration of a wild-type MCC gene.

Mutant MCC genes or gene products can also be detected in other human body samples, such as, serum, stool, urine and sputum. The same techniques discussed above for detection of mutant MCC genes or gene products in tissues can be applied to other body samples. Cancer cells are sloughed off from tumors and appear in such body samples. In addition, the MCC gene product itself may be secreted into the extracellular space and found in these body samples even in the absence of cancer cells. By screening such body samples, a simple early diagnosis can be achieved for many types of cancers. In addition, the progress of chemotherapy or radiotherapy can be monitored more easily by testing such body samples for mutant MCC genes or gene products.

The methods of diagnosis of the present invention are applicable to any tumor in which MCC has a role in tumorigenesis. Deletions of chromosome arm 5q have been observed in tumors of lung, breast, colon, rectum, bladder, liver, sarcomas, stomach and prostate, as well as in leukemias and lymphomas. Thus these are likely to be tumors in which MCC has a role. The diagnostic method of the present invention is useful for clinicians so that they can decide upon an appropriate course of treatment. For example, a tumor displaying alteration of both MCC alleles might suggest a more aggressive therapeutic regimen than a tumor displaying alteration of only one MCC allele.

The primer pairs of the present invention are useful for determination of the nucleotide sequence of the MCC gene using the polymerase chain reaction. The pairs of single stranded DNA primers can be annealed to sequences within or surrounding the MCC gene on chromosome 5q in order to prime amplifying DNA synthesis of the MCC gene itself. A complete set of these primers allows synthesis of all of the nucleotides of the MCC gene coding sequences, i.e., the exons. The set of primers preferably allows synthesis of both intron and exon sequences. Allele specific primers can also be used. Such primers anneal only to particular MCC mutant alleles, and thus will only amplify a product in the presence of the mutant allele as a template.

In order to facilitate subsequent cloning of amplified sequences, primers may have restriction enzyme site sequences appended to their 5' ends. Thus, all nucleotides of the primers are derived from MCC sequences or sequences adjacent to MCC except the few nucleotides necessary to form a restriction enzyme site. Such enzymes and sites are well known in the art. The primers themselves can be synthesized using techniques which are well known in the art. Generally, the primers can be made using synthesizing machines which are commercially available. Given the sequence of the MCC open reading frame shown in FIG. 3, design of particular primers is well within the skill of the art.

The nucleic acid probes provided by the present invention are useful for a number of purposes. They can be used in Southern hybridization to genomic DNA and in the RNase protection method for detecting point mutations already discussed above. The probes can be used to detect PCR amplification products. They may also be used to detect mismatches with the MCC gene or mRNA using other techniques. Mismatches can be detected using either enzymes (e.g., S1 nuclease), chemicals (e.g., hydroxylamine or osmium tetroxide and piperidine), or changes in electrophoretic mobility of mismatched hybrids as compared to totally matched hybrids. These techniques are known in the art. See, Cotton, supra, Shenk, supra, Myers, supra, Winter, supra, and Novack et al., Proc. Natl. Acad. Sci. USA, vol. 83, p. 586, 1986. Generally, the probes are complementary to MCC gene coding sequences, although probes to certain introns are also contemplated. An entire battery of nucleic acid probes is used to compose a kit for detecting alteration of wild-type MCC genes. The kit allows for hybridization to the entire MCC gene. The probes may overlap with each other or be contiguous.

If a riboprobe is used to detect mismatches with mRNA, it is complementary to the mRNA of the human wild-type MCC gene. The riboprobe thus is an anti-sense probe in that it does not code for the MCC protein because it is of the opposite polarity to the sense strand. The riboprobe generally will be labeled with a radioactive, colorimetric, or fluorometric materials, which can be accomplished by any means known in the art. If the riboprobe is used to detect mismatches with DNA it can be of either polarity, sense or anti-sense. Similarly, DNA probes also may be used to detect mismatches.

Nucleic acid probes may also be complementary to mutant alleles of MCC gene. These are useful to detect similar mutations in other patients on the basis of hybridization rather than mismatches. These are discussed above and referred to as allele-specific probes. As mentioned above, the MCC probes can also be used in Southern hybridizations to genomic DNA to detect gross chromosomal changes such as deletions and insertions. The probes can also be used to select cDNA clones of MCC genes from tumor and normal tissues. In addition, the probes can be used to detect MCC mRNA in tissues to determine if expression is diminished as a result of alteration of wild-type MCC genes. Provided with the MCC coding sequence shown in FIG. 3 (SEQ ID NO:1), design of particular probes is well within the skill of the ordinary artisan.

According to the present invention a method is also provided of supplying wild-type MCC function to a cell which carries mutant MCC alleles. Supplying such function should suppress neoplastic growth of the recipient cells. The wild-type MCC gene or a part of the gene may be introduced into the cell in a vector such that the gene remains extrachromosomal. In such a situation the gene will be expressed by the cell from the extrachromosomal location. If a gene portion is introduced and expressed in a cell carrying a mutant MCC allele, the gene portion should encode a part of the MCC protein which is required for non-neoplastic growth of the cell. More preferred is the situation where the wild-type MCC gene or a part of it is introduced into the mutant cell in such a way that it recombines with the endogenous mutant MCC gene present in the cell. Such recombination requires a double recombination event which results in the correction of the MCC gene mutation. Vectors for introduction of genes both for recombination and for extrachromosomal maintenance are known in the art and any suitable vector may be used. Methods for introducing DNA into cells such as electroporation, calcium phosphate co-precipitation and viral transduction are known in the art and the choice of method is within the competence of the routineer. Cells transformed with the wild-type MCC-gene can be used as model systems to study cancer remission and drug treatments which promote such remission.

Polypeptides which have MCC activity can be supplied to cells which carry mutant or missing MCC alleles. The sequence of the MCC protein is disclosed in FIG. 8 (SEQ ID NO:2). Protein can be produced by expression of the cDNA sequence in bacteria, for example, using known expression vectors. Alternatively, MCC can be extracted from MCC-producing mammalian cells such as brain cells. In addition, the techniques of synthetic chemistry can be employed to synthesize MCC protein. Any of such techniques can provide the preparation of the present invention which comprises the MCC gene product having the sequence shown in FIG. 3 (SEQ ID NO:2). The preparation is substantially free of other human proteins. This is most readily accomplished by synthesis in a microorganism or in vitro. Active MCC molecules can be introduced into cells by microinjection or by use of liposomes, for example. Alternatively, some such active molecules may be taken up by cells, actively or by diffusion. Extracellular application of MCC gene product may be sufficient to affect tumor growth. Supply of molecules with MCC activity should lead to a partial reversal of the neoplastic state. Other molecules with MCC activity may also be used to effect such a reversal, for example peptides, drugs, or organic compounds.

The present invention also provides a preparation of antibodies immunoreactive with a human MCC protein. The antibodies may be polyclonal or monoclonal and may be raised against native MCC protein, MCC fusion proteins, or mutant MCC proteins. The antibodies should be immunoreactive with MCC epitopes, preferably epitopes not present on other human proteins. In a preferred embodiment of the invention the antibodies will immunoprecipitate MCC proteins from solution as well as react with MCC protein on Western or immunoblots of polyacrylamide gels. In another preferred-embodiment, the antibodies will detect MCC proteins in parrafin or frozen tissue sections, using immunocytochemical techniques. Techniques for raising and purifying antibodies are well known in the art and any such techniques may be chosen to achieve the preparation of the invention.

Predisposition to cancers can be ascertained by testing normal tissues of humans for mutations of MCC gene. For example, a person who has inherited a germline MCC mutation would be prone to develop cancers. This can be determined by testing DNA from any tissue of the person's body. Most simply, blood can be drawn and DNA extracted from the cells of the blood. In addition, prenatal diagnosis can be accomplished by testing fetal cells or amniotic fluid for mutations of the MCC gene. Alteration of a wild-type MCC allele, whether for example, by point mutation or by deletion, can be detected by any of the means discussed above.

Molecules of cDNA according to the present invention are intron-free, MCC gene coding molecules. They can be made by reverse transcriptase using the MCC mRNA as a template. These molecules can be propagated in vectors and cell lines as is known in the art. Such molecules have the sequence shown in SEQ ID NO: 1. The cDNA can also be made using the techniques of synthetic chemistry given the sequence disclosed herein.

A short region of homology has been identified between MCC and the human m3 muscarinic acetylcholine receptor (mAChR). This homology was largely confined to 19 residues in which the carboxy-terminal 6 amino acids (KELAGL) were identical (See FIG. 5 and SEQ ID NO: 11). Initially, it was not known whether this homology was significant, because many other proteins had higher levels of global homology (though few had six contiguous amino acids in common). During a search for mutations, however, a study on the sequence elements controlling G protein activation by mAChR subtypes was published (Lechleiter et al., EMBO J., p. 4381 (1990)). It was shown that a 21 amino acid region from the m3 mAChR completely mediated G protein specificity when substituted for the 21 amino acids of m2 mAChR at the analogous protein position. These 21 residues overlapped the 19 amino acid homology between MCC and m3 mAChR (FIG. 5). A ten residue deletion (FIG. 5, domain A), which included the two amino-terminal amino acids of the KELAGL motif, completely altered the kinetics and magnitude of the G protein mediated response. Moreover, a 9-residue subdomain (FIG. 5, domain B) which included the 4 carboxy-terminal amino acids of KELAGL, was sufficient for specifying the activation of the m3 G protein pathway when transferred to the m2 mAChR.

This connection between MCC and the. G protein activating region of mAChR is intriguing in light of previous investigations relating G proteins to cancer. For example, the RAS oncogenes, which are often mutated in colorectal cancers (Vogelstein, et al., N. Engl. J. Med., vol. 319, pg. 525 (1988); Bos et al., Nature vol. 327, pg. 293 (1987)), are members of the G protein family (Bourne, et al., Nature, vol. 348, pg. 125 (1990)) as is an in vitro transformation suppressor (Noda et al., Proc. Natl. Acad. Sci. USA, vol 86, pg. 162 (1989)) and genes mutated in hormone producing tumors (Candis et al., Nature, vol. 340, pg. 692 (1989); Lyons et al., Science, vol. 249, pg. 655 (1990)). Additionally, the gene responsible for neurofibromatosis (presumably a tumor suppressor gene) has been shown to activate the GTPase activity of RAS (Xu et al., Cell, vol. 63, pg. 835 (1990); Martin et al., Cell, vol. 63, pg. 843 (1990); Ballester et al., Cell, vol. 63, pg. 851 (1990)). Another interesting link between G proteins and colon cancer involves the drug sulindac. This agent has been shown to inhibit the growth of benign colon tumors in patients with FAP, presumably by virtue of its activity as a cyclooxygenase inhibitor (Waddell et al., J. Surg. Oncology 24(1), 83 (1983); Wadell, et al., Am. J. Surg., 157(1), 175 (1989); Charneau et al., Gastroenterologie Clinique at Biologique 14(2), 153 (1990)). Cyclooxygenase is required to convert arachidonic acid to prostaglandins and other biologically active molecules. G proteins are known to regulate phospholipase A2 activity, which generates arachidonic acid from phosphplipids (Role et al., Proc. Natl. Acad. Sci. USA, vol. 84, pg. 3623 (1987); Kurachi et al., Nature, vol. 337, pg. 555 (1989)). Therefore we propose that wild-type MCC protein functions by interacting with a G protein and is involved in phospholipid metabolism.

The following are provided for exemplification purposes only and are not intended to limit the scope of the invention which has been described in broad terms above.

EXAMPLE 1

This example demonstrates the detection of a somatic cell gene rearrangement occurring in chromosome 5q21 in a colorectal carcinoma.

We mapped allele losses which occur in over 30% of sporadic cancers using restriction fragment length polymorphisms (RFLP) markers. We found that the region of common loss seems to be centered at an RFLP detected by cosmid 5.71.

Figure 1B:
Figure 1C:
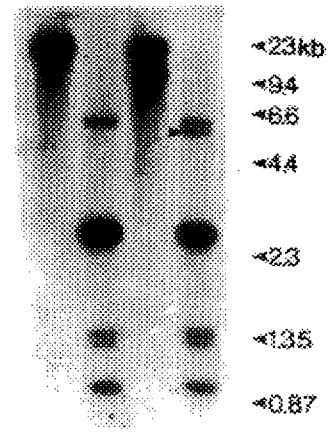

Portions of cosmid 5.71 were subcloned and used as probes to screen a panel of 150 colorectal carcinomas by Southern blot analysis. We found one tumor (T14) which contained an 11 kb EcoRI fragment in addition to the 20 kb EcoRI fragment seen in DNA from normal individuals. The 11 kb fragment was not present in DNA isolated from normal cells from the same patient (FIG. 1, Panel A).

The new EcoRI fragment was cloned[1]/, and used to probe Southern blots with DNA from tumor T14. The 11 kb clone hybridized to the abnormal 11 kb EcoRI fragment and to the normal 20 kb EcoRI fragment in the tumor as expected (FIG. 1, Panel B). Moreover, the 11 kb clone detected new fragments in tumor T14 DNA upon digestion with other restriction endonucleases (including PstI [FIG. 1, Panel C]; Hind III and EcoRV).

[1]/EcoRI fragments of T14 tumor DNA were ligated to lambda DASH vector arms (Stratagene). Following packaging and infection of C600 E. coli cells, hybridizing clones were identified with a probe derived from 5.71 sequences.

Restriction mapping and partial sequencing of the 11 kb clone showed that Its left end was derived from the 20 kb EcoRI fragment which contained 5.71 sequences. The right end of the 11 kb fragment was derived from sequences which were not contiguous with the left end in normal genomic DNA. Use of a 400 bp probe from the right end of the 11 kb fragment showed that the non-contiguous sequences were also derived from chromosome 5, but from a position separated by at least 100 kb from the left end of the 11 kb EcoRI fragment. Thus a rearrangement had occurred in the tumor which resulted in the juxtaposition of sequences which were normally far apart.

EXAMPLE 2

This example documents our efforts to locate a gene affected by the rearrangement found in colorectal tumor T14.

Based on the hypothesis that human genes that are expressed are evolutionarily conserved among mammalian species, we looked for genomic sequences in rat which shared homology with the 5.71 cosmid. Several subclones of the 5.71 cosmid were used in Southern blot analysis of rodent DNA. Cross-species hybridization was performed at 55 degrees as described in Vogelstein, et al., Cancer Research, vol. 47, pg. 4806 (1987), and washed for 45 minutes at 55 degrees in 45 mM sodium chloride, 2 mM sodium citrate, 0.8 mM Tris, HCl pH 7.5, 0.1% sodium dodecyl sulfate. We identified two subclones (5.71–5 and 5.71–3) that cross-hybridized under reduced stringency. However, attempts to use these conserved sequences to detect expressed human genes by Northern blotting and cDNA library screening of over $3 \times 10^6$ colon or brain cDNA clones were unsuccessful.

EXAMPLE 3

This example demonstrates the identification of an expressed human gene near the cosmid 5.71 RFLP marker.

We sequenced parts of the human subclones demonstrating cross-species hybridization, but found it impossible to predict exons from this sequence information alone. We therefore cloned the cross-hybridizing rat fragments and determined their sequence as well. A rat genomic library in the lambda DASH vector (Stratagene) was probed with $^{32}$P-labelled 5.71-3 and 5.71-5 sequences. Cross-hybridizing restriction fragments of these phage clones were subcloned into plasmid vectors and sequenced to derive the homologies shown in FIG. 2. Sequencing was performed with unmodified T7 polymerase as described by G. Del Sal, G. Manfioletti and C. Schneider, Biotechniques 7:514, 1989.

Through comparison of the sequences of the corresponding rat and human regions, one putative exon from subclone 5.71-3 and one from subclone 5.71-5 were identified (FIG. 2). Each contained an open reading frame (ORF) that was preceded and followed by splice acceptor and donor sites that were conserved between species. The predicted ORF's from the rat and human exons were 96% identical at the amino acid level and 89% identical at the nucleotide level, with most of the nucleotide differences occurring at the third position of codons. The two putative exons are separated in genomic DNA by over 2 kb.

Primers were derived from the two putative exons. PCR performed with these primers, using cDNA as template, allows detection of putative exons if they are joined by RNA splicing within cells. Contaminating genomic DNA in the RNA preparation does not interfere with this assay, since the Intervening Intron(s) results in much longer PCR products from genomic DNA than that obtained from the spliced RNA.

We did not initially know the orientation of the putative exons with respect to one another and therefore designed two sets of primers for the exon-connection scheme. One set (primers P1 and P4; FIG. 2) would have resulted in a PCR product if the exon in 5.71-5 was upstream of that in 5.71-3. The other set (primers P2 and P3; FIG. 2) would have allowed detection of a PCR product if the exons were in the reverse orientation.

PCR was performed as described in Baker et al., Cancer Research, vol. 50, pg. 7717 (1990), using 35 cycles of: 95 degrees C. for 0.5 minutes, 55 degrees C. for 2 minutes, and 70 degrees C. for 2 minutes. We found that only the first set (primers P1 and P4) results in a PCR product using cDNA derived from mRNA of normal human colon as template. The PCR product was exactly the size (226 bp) expected if direct splicing of the two putative exons had occurred at the splice sites identified in the human and rat genomic DNA sequences. Cloning and sequencing of the PCR product confirmed that it represented the result of a direct splice between the 5.71-5 and 5.71-3 exons. This spliced product produced an in-frame fusion of the ORF's from each exon. We concluded that these sequences did indeed represent an expressed gene, hereinafter referred to as the MCC gene for mutated in colorectal cancer. Using the exon-connection strategy, we found that MCC was expressed in most normal tissues of the rat (e.g., colon, brain, stomach, lung, liver, kidney, bladder, heart).

EXAMPLE 4

This example demonstrates the isolation and sequencing of the human MCC cDNA from brain.

The PCR product amplified using human cDNA as a template was then labelled and used as a probe to screen a cDNA library from normal human brain. Brain was chosen because the exon-connection assay suggested that MCC was expressed at high levels in this tissue. The cDNA library was constructed from human brain mRNA as described in U. Gubler and B. J. Hoffman, Gene 25, 263 (1983) and the Lambda Zap vector (Stratagene). $1.5 \times 10^6$ plaques were screened with the PCR product connecting the 5.71-3 and 5.71-5 exons (see FIG. 2.)

Three clones were identified in the $1.5 \times 10^6$ plaques In the initial screen. The ends of these three clones were then used to re-screen the library, and a series of seven overlapping cDNA clones were finally isolated and ordered. Sequence analysis of these clones indicated that they encompassed 4,180 bp of MCC mRNA and contained an ORF of 2,511 bp (FIG. 3). The first methionine of the ORF (nucleotide 220) was preceded by in frame stop codons upstream and conformed reasonably well to the consensus initiation site defined by Kozak (Nucleic Acids Research, vol. 15, pg. 8125 (1987)). If translation initiation occurs at this methionine, the sequence predicts an 829 amino acid product (93 kd) enceded from nucleotide 220 to 2707. The ORF was surrounded by at least 200 bp of 5' untranslated sequence and 1450 bp of 3' untranslated sequence. There was no evidence of a polyadenylylation tract at the 3' end of any clone. cDNA probes detected RNAs of several seizes (3-10 kb) on Northern blots; we do not know whether these other transcripts represent alternatively spliced forms of the MCC gene or related genes from other loci.

Searches of nucleotide databases (EMBL version 25, Genbank version 66) indicated that this sequence has not been previously reported. Searches of amino acid databases (P.I.R. version 25, SWISS-Protein version 16) with the predicted MCC protein (829 amino acids) also failed to reveal any extensive homologies. However, we noted a 19 amino acid region of homology between MCC and the G-protein-coupled muscarinic acetylcholine receptor of humans and pigs.

EXAMPLE 5

This example demonstrates that somatic mutations occur within the MCC gene in colorectal carcinoma tissue.

When the sequences of MCC were compared with those of genomic clones from tumor T14 it was found that the boundary of the rearrangement in this tumor was within the MCC gene, occurring in the intron just distal to the exon containing nucleotides 534 to 676. As noted above, the novel 11 kb restriction fragment represented the joining of sequences on chromosome 5 normally separated by more than 100 kb. This 100 kb stretch contained several exons of the MCC gene. Thus, the MCC gene was disrupted by a genetic alteration which removed exons from the rearranged MCC gene in this tumor.

To search for other more subtle genetic alterations of MCC, we employed the polymerase chain reaction to amplify exons of the MCC gene from colorectal cancers. These sequences were then analyzed for mutations by an RNase protection assay which was modified to allow rapid testing of multiple samples. In brief, the sequence of an exon and surrounding intron was determined and used to design primers for the amplification of the exon and surrounding splice sites. The exon was then amplified from tumor DNA using PCR.

The sequences of exon boundaries were derived following the screening of human genomic DNA libraries with MCC cDNA probes. Positively hybridizing clones were isolated and small fragments (0.2–3 kb) subcloned and sequenced. Primers for amplifying the exons were chosen outside of the splice sites and were as follows: 5'-GAATTCATCAGCACTTCT-3' (SEQ ID NO:3) and 5'-CAGCTCCAAGATGGAGGG-3' (SEQ ID NO:4) for the exon containing nucleotides 391 to 533, 5'-GGCCCCATGTGCTTTGTT-3' (SEQ ID NO:5) and 5'-AGAGGGACTCTGGAGACA-3' (SEQ ID NO:6) for the exon containing nucleotides 1575 to 1678, 5'-ATGTTGATTAATCCGTTGGC-3' (SEQ ID NO:7) and 5'-ACCCCAGAGCAGAAGGCT-3' (SEQ ID NO: 8) for the exon containing nucleotides 1679–1862, 5'-GGCCTAACTGGAATGTGT-3' (SEQ ID NO: 9) and 5'-GCCCAGATAAACACCAGC-3' (SEQ ID NO:10) for the exon containing nucleotides 2305 to 2405. PCR was carried out as described above.

The resulting PCR products were hybridized to in vitro generated RNA probes representing normal MCC sequences. The hybrids were digested with RNase A, which can cleave at single base pair mismatches within DNA-RNA hybrids, and these cleavage products visualized following denaturing gel electrophoresis. Two separate RNase protection analyses were performed for each exon, one with the sense and one with the antisense strand as labeled transcript. Under these conditions approximately 50% of all point mutations are detectable. R. M. Myers and T. Maniatis, Cold Spring Harbor Symposia on Quantitative Biology, 51,275 (1986).

The RNAse protection assay was performed as described by Winter et al., Proc. Natl. Acad. Sci. USA, vol. 82, pg. 7575 (1985) with the following modifications: Hybridizations were carried out in 9 ul of hybridization solution containing 1 ul of the appropriate PCR reaction and $^{32}$P labeled transcript (200,000 dpm) for 2 hours at 50 degrees C. RNase treatment was initiated by addition of 90 ul of RNase solution (0.2M NaCl, 0.1M LiCl, 20 mM Tris-HCl, pH 7.5, 1 mM EDTA, 25 ug/ml RNase A) and incubated 1 hour at 37 degrees C. RNase treatment was terminated by the addition of proteinase K solution (5 mg/ml proteinase K in 10% SDS) and incubated 1 hour at 37 degrees C. The solution was then extracted one time with PC9 (3 parts phenol and 4 parts chloroform equilibrated with 2 parts 0.5M Tris-HCl, pH 9.0, 10 mM EDTA, 10 mM NaCl) and 20 ul of the aqueous phase was collected and combined wtih 20 ul of loading buffer (0.3% W/V xylene cyanol, 0.3% W/V bromophenol blue in formamide). The samples were then heated at 94 degrees C. for 4 minutes and loaded directly on a denaturing polyacrylamide gel. Two separate assays were performed for each exon, one with each strand as labeled transcript.

The first exon (containing nucleotides 391 to 533) of four tested showed no variants among 100 colorectal tumors tested. Analysis of the exon containing nucleotides 1575 to 1678 identified five tumors with identical variations in their RNase protection pattern. Cloning and sequencing of the variant PCR product from two of the five tumors indicated that it resulted from a C to T transition at nucleotide 1676 which resulted in a coding change from proline to leucine. This variant presumably represents a polymorphism, as it was found in five individuals and was present in DNA from the normal tissue of two of the five patients whose tumors showed the variant (the other three were not tested).

Analysis of a third exon (containing nucleotides 2305 to 2405) identified a single tumor (T91) with a unique RNase protection pattern. This abnormal RNase protection pattern was not seen in DNA isolated from normal tissue from the same individual (FIG. 4). This indicates that the altered RNase protection pattern was the result of a somatic mutation. Cloning and sequencing of the T91 tumor PCR product indicated that it had a C to T transition at nucleotide 2312 that resulted in a ceding change from alanine to valine. Although this is a relatively conservative amino acid substitution, the identical amino acid change has been shown to inactivate the p53 tumor suppressor gene. S. J. Baker et al., Science, vol. 244, pg. 217 (1989); S. J. Baker et al., Science, vol. 249, pg. 912 (1990).

Analysis of a fourth exon (containing nucleotides 1679 to 1862) identified a single tumor (T35) with a unique RNase protection pattern. Examination of DNA isolated from normal tissue of the same individual indicated that this altered RNase protection pattern was also the result of a somatic mutation (FIG. 4). Cloning and sequencing of the T35 PCR product indicated that it had a G to A transition at nucleotide 1736 resulting in a coding change from arginine to glutamine.

---

We claim:

1. A method of supplying wild-type MCC gene function to a cell which has lost said gene function by virtue of a mutation in an MCC gene, comprising:

introducing a wild-type MCC gene into a cell which has lost said gene function such that said wild-type MCC gene is expressed in the cell.

2. The method of claim 1 wherein the wild-type MCC gene introduced recombines with the endogenous mutant MCC gene present in the cell by a double recombination event to correct the MCC gene mutation.

3. A method of supplying wild-type MCC gene function to a cell which has a mutation in an MCC gene, comprising:

introducing a portion of a wild-type MCC gene into a cell which has lost said gene function such that said portion is expressed in the cell, said portion comprising a part of the wild-type MCC gene which contains the mutation in the cell.

\* \* \* \* \*

SEQUENCE LISTING ( 1 ) GENERAL INFORMATION:

( i i i ) NUMBER OF SEQUENCES: 19

( 2 ) INFORMATION FOR SEQ ID NO:1:

( i ) SEQUENCE CHARACTERISTICS:
        ( A ) LENGTH: 4181 base pairs
        ( B ) TYPE: nucleic acid
        ( C ) STRANDEDNESS: double
        ( D ) TOPOLOGY: linear ( i i ) MOLECULE TYPE: cDNA ( i i i ) HYPOTHETICAL: NO ( i v ) ANTI-SENSE: NO ( v i ) ORIGINAL SOURCE:
        ( A ) ORGANISM: Homo sapiens -continued (viii) POSITION IN GENOME:
    (A) CHROMOSOME/SEGMENT: 5q21

(xi) SEQUENCE DESCRIPTION: SEQ ID NO:1:

```
CCTCCTGCAG CAATGGCTCG TCCGTGAAAC GCGAGCCACG GCTGCTCTTT TTAAGAGTGC    60
CTGCATCCTC CGTTTGCGCT TCGCAACTGT CCTGGGTGAA AATGGCTGTC TAGACTAAAA   120
TGTGGCAGAA GGGACCAAGC AGTGGATATT GAGCCTGTGA AGTCCAACTC TTAAGCTCCG   180
AGACCTGGGG GACTGAGAGC CCAGCTCTGA AAAGTGCATC ATGAATTCCG GAGTTGCCAT   240
GAAATATGGA AACGACTCCT CGGCCGAGCT GAGTGAGCTC CATTCAGCAG CCCTGGCATC   300
ACTAAAGGGA GATATAGTGG AACTTAATAA ACGTCTCCAG CAAACAGAGA GGGAACGGGA   360
CCTTCTGGAA AAGAAATTGG CCAAGGCACA GTGCGAGCAG TCCCACCTCA TGAGAGAGCA   420
TGAGGATGTC CAGGAGCGAA CGACGCTTCG CTATGAGGAA CGCATCACAG AGCTCCACAG   480
CGTCATTGCG GAGCTCAACA AGAAGATAGA CCGTCTGCAA GGCACCACCA TCAGGGAGGA   540
AGATGAGTAC TCAGAACTGC GATCAGAACT CAGCCAGAGC CAACACGAGG TCAACGAGGA   600
CTCTCGAAGC ATGGACCAAG ACCAGACCTC TGTCTCTATC CCCGAAAACC AGTCTACCAT   660
GGTTACTGCT GACATGGACA ACTGCAGTGA CCTGAACTCA GAACTGCAGA GGGTGCTGAC   720
AGGGCTGGAG AATGTTGTCT GCGGCAGGAA GAAGAGCAGC TGCAGCCTCT CCGTGGCCGA   780
GGTGGACAGG CACATTGAGC AGCTCACCAC AGCCAGCGAG CACTGTGACC TGGCTATTAA   840
GACAGTCGAG GAGATTGAGG GGGTGCTTGG CCGGGACCTG TATCCCAACC TGGCTGAAGA   900
GAGGTCTCGG TGGAGAAGG AGCTGGCTGG GCTGAGGGAA GAGAATGAGA GCCTGACTGC   960
CATGCTGTGC AGCAAAGAGG AAGAACTGAA CCGGACTAAG GCCACCATGA ATGCCATCCG  1020
GGAAGAGCGG GACCGGCTCC GGAGGCGGGT CAGAGAGCTT CAAACTCGAC TACAGAGCGT  1080
GCAGGCCACA GGTCCCTCCA GCCCTGGCCG CCTCACTTCC ACCAACCGCC CGATTAACCC  1140
CAGCACTGGG GAGCTGAGCA CAAGCAGCAG CAGCAATGAC ATTCCCATCG CCAAGATTGC  1200
TGAGAGGGTG AAGCTATCAA AGACAAGGTC CGAATCGTCA TCATCTGATC GGCCAGTCCT  1260
GGGCTCAGAA ATCAGTAGCA TAGGGGTATC CAGCAGTGTG GCTGAACACC TGGCCCACTC  1320
ACTTCAGGAC TGCTCCAATA TCCAAGAGAT TTTCCAAACA CTCTACTCAC ACGGATCTGC  1380
CATCTCAGAA AGCAAGATTA GAGAGTTTGA GGTGGAAACA GAACGGCTGA ATAGCCGGAT  1440
TGAGCACCTC AAATCCCAAA ATGACCTCCT GACCATAACC TTGGAGGAAT GTAAAAGCAA  1500
TGCTGAGAGG ATGAGCATGC TGGTGGGAAA ATACGAATCC AATGCCACAG CGCTGAGGCT  1560
GGCCTTGCAG TACAGCGAGC AGTGCATCGA AGCCTACGAA CTCCTCCTGG CGCTGGCAGA  1620
GAGTGAGCAG AGCCTCATCC TGGGGCAGTT CCGAGCGGCG GGCGTGGGGT CCTCCCCTGG  1680
AGACCAGTCG GGGGATGAAA ACATCACTCA GATGCTCAAG CGAGCTCATG ACTGCCGGAA  1740
GACAGCTGAG AACGCTGCCA AGGCCCTGCT CATGAAGCTG GACGGCAGCT GTGGGGAGC  1800
CTTTGCCGTG GCCGGCTGCA GCGTGCAGCC CTGGGAGAGC CTTTCCTCCA ACAGCCACAC  1860
CAGCACAACC AGCTCCACAG CCAGTAGTTG CGACACCGAG TTCACTAAAG AAGACGAGCA  1920
GAGGCTGAAG GATTATATCC AGCAGCTCAA GAATGACAGG GCTGCGGTCA AGCTGACCAT  1980
GCTGGAGCTG GAAAGCATCC ACATCGATCC TCTCAGCTAT GACGTCAAGC CTCGGGGAGA  2040
CAGCCAGAGG CTGGATCTGG AAAACGCAGT GCTTATGCAG GAGCTCATGG CCATGAAGGA  2100
GGAGATGGCC GAGTTGAAGG CCCAGCTCTA CCTACTGGAG AAAGAGAAGA AGGCCCTGGA  2160
GCTGAAGCTG AGCACGCGGG AGGCCCAGGA GCAGGCCTAC CTGGTGCACA TTGAGCACCT  2220
GAAGTCCGAG GTGGAGGAGC AGAAGGAGCA GCGGATGCGA TCCCTCAGCT CCACCAGCAG  2280
```

```
CGGCAGCAAA GATAAACCTG GCAAGGAGTG TGCTGATGCT GCCTCCCCAG CTCTGTCCCT     2340
AGCTGAACTC AGGACAACGT GCAGCGAGAA TGAGCTGGCT GCGGAGTTCA CCAACGCCAT     2400
TCGTCGAGAA AAGAAGTTGA AGGCCAGAGT TCAAGAGCTG GTGAGTGCCT TGGAGAGACT     2460
CACCAAGAGC AGTGAAATCC GACATCAGCA ATCTGCAGAG TTCGTGAATG ATCTAAAGCG     2520
GGCCAACAGC AACCTGGTGG CTGCCTATGA GAAAGCAAAG AAAAAGCATC AAAACAAACT     2580
GAAGAAGTTA GAGTCGCAGA TGATGGCCAT GGTGGAGAGA CATGAGACCC AAGTGAGGAT     2640
GCTCAAGCAA AGAATAGCTC TGCTAGAGGA GGAGAACTCC AGGCCACACA CCAATGAAAC     2700
TTCGCTTTAA TCAGCACTCA CGCACCGGAG TTCTGCCCAT GGGAAGTAAA CTGCAGCAGG     2760
CCACTGGGGA CAGAAGGGCC CATGTACTTG TTGGGAGGAG GAGGAAAGGG AAGGCTGGCA     2820
GGTAGGTCGG CACTTGGACA ATGGAGTGCC CCAACTCAAC CCTTGGGGTG ACTGGCCATG     2880
GTGACATTGT GGACTGTATC CAGAGGTGCC CGCTCTTCCC TCCTGGGCCC ACAACAGCGT     2940
GTAAACACAT GTTCTGTGCC TGCTCAGCAG AGCCTCGTTT CTGCTTTCAG CACTCACTCT     3000
CCCCCTCCTC TTCTGGTCTG GCGGCTGTGC ATCAGTGGGA TCCCAGACAT TTGTTTCTGT     3060
AAGATTTTCC ATTGTATCCT CTTTTTGGTA GATGCTGGGC TCATCTTCTA GAATCTCGTT     3120
TCTCCTCTTT CCTCCTGCTT CATGGGAAAA CAGACCTGTG TGTGCCTCCA GCATTTAAAA     3180
GGACTGCTGA TTTGTTTACT ACAGCAAGGC TTTGGTTTCC AAGTCCCGGG TCTCAACTTT     3240
AAGATAGAGG CGGCCATAAG AGGTGATCTC TGGGAGTTAT AGGTCATGGG AAGAGCGTAG     3300
ACAGGTGTTA CTTACAGTCC CAGATACACT AAAGTTACAA ACAGACCACC ACCAGGACTG     3360
TGCCTGAACA ATTTTGTATT GAGAGAATAA AAACTTCCTT CAATCTTCAT TTTGGAGGCA     3420
GGGCTGGGAA GGGAGCGCTC TCTTGATTCT GGGATTTCTC CCTCTCAGTG GAGCCTTATT     3480
AATATCCAAG ACTTAGAGCT GGGAATCTTT TTGATACCTG TAGTGGAACT AAAATTCTGT     3540
CAGGGGTTTC TTCAAGAGCT GAGAAACATT ATTAGCACTT CCCGCCCCAG GGCACTACAT     3600
AATTGCTGTT CTGCTGAATC AAATCTCTTC CACATGGGTG CATTTGTAGC TCTGGACCTG     3660
TCTCTACCTA AGGACAAGAC ACTGAGGAGA TACTGAACAT TTGCAAAAC TTATCACGCC     3720
TACTTAAGAG TGCTGTGTAA CCCCCAGTTC AAGACTTAGC TCCTGTTGTC ATGACGGGGA     3780
CAGAGTGAGG GAATGGTAGT TAAGGCTTCT TTTTTGCCCC CAGATACATG GTGATGGTTA     3840
GCATATGGTG CTTAAAAGGT TAAATTTCAA GCAAATGCT TACAGGGCTA GGCAGTACCA     3900
AAGTAACTGA ATTATTTCAG GAAGGTCTTC AATCTTAAAA CAAATTCATT ATTCTTTTTC     3960
AGTTTTACCT CTTCTCTCTC AGTTCTACAC TGATACACTT GAAGGACCAT TTACTGTTTT     4020
TTTCTGTAGC ACCAGAGAAT CCATCCAAAG TTCCCTATGA AAAATGTGTT CCATTGCCAT     4080
AGCTGACTAC AAATTAAAGT TGAGGAGGTT TCTGCATAGA GTCTTTATGT CCATAAGCTA     4140
CGGGTAGGTC TATTTTCAGA GCATGATACA AATTCCACAG G                       4181
```

( 2 ) INFORMATION FOR SEQ ID NO:2:

( i ) SEQUENCE CHARACTERISTICS:
        ( A ) LENGTH: 829 amino acids
        ( B ) TYPE: amino acid
        ( C ) STRANDEDNESS: single
        ( D ) TOPOLOGY: linear ( i i ) MOLECULE TYPE: protein ( i i i ) HYPOTHETICAL: YES ( i v ) ANTI-SENSE: NO ( v i ) ORIGINAL SOURCE:
  ( A ) ORGANISM: Homo sapiens ( x i ) SEQUENCE DESCRIPTION: SEQ ID NO:2:

| | | | | | | | | | | | | | | |
|---|---|---|---|---|---|---|---|---|---|---|---|---|---|---|
| Met<br>1 | Asn | Ser | Gly | Val<br>5 | Ala | Met | Lys | Tyr | Gly<br>10 | Asn | Asp | Ser | Ser | Ala<br>15 | Glu |
| Leu | Ser | Glu | Leu<br>20 | His | Ser | Ala | Ala | Leu<br>25 | Ala | Ser | Leu | Lys | Gly<br>30 | Asp | Ile |
| Val | Glu | Leu<br>35 | Asn | Lys | Arg | Leu | Gln<br>40 | Thr | Glu | Arg | Glu<br>45 | Arg | Asp | Leu |
| Leu | Glu<br>50 | Lys | Lys | Leu | Ala | Lys<br>55 | Ala | Gln | Cys | Glu | Gln<br>60 | Ser | His | Leu | Met |
| Arg<br>65 | Glu | His | Glu | Asp | Val<br>70 | Gln | Glu | Arg | Thr | Thr<br>75 | Leu | Arg | Tyr | Glu | Glu<br>80 |
| Arg | Ile | Thr | Glu | Leu<br>85 | His | Ser | Val | Ile | Ala<br>90 | Glu | Leu | Asn | Lys | Lys<br>95 | Ile |
| Asp | Arg | Leu | Gln<br>100 | Gly | Thr | Thr | Ile | Arg<br>105 | Glu | Glu | Asp | Glu | Tyr<br>110 | Ser | Glu |
| Leu | Arg | Ser<br>115 | Glu | Leu | Ser | Gln<br>120 | Ser | Gln | His | Glu | Val<br>125 | Asn | Glu | Asp | Ser |
| Arg | Ser<br>130 | Met | Asp | Gln | Asp | Gln<br>135 | Thr | Ser | Val | Ser | Ile<br>140 | Pro | Glu | Asn | Gln |
| Ser<br>145 | Thr | Met | Val | Thr | Ala<br>150 | Asp | Met | Asp | Asn | Cys<br>155 | Ser | Asp | Leu | Asn | Ser<br>160 |
| Glu | Leu | Gln | Arg | Val<br>165 | Leu | Thr | Gly | Leu | Glu<br>170 | Asn | Val | Val | Cys | Gly<br>175 | Arg |
| Lys | Lys | Ser | Ser<br>180 | Cys | Ser | Leu | Ser | Val<br>185 | Ala | Glu | Val | Asp | Arg<br>190 | His | Ile |
| Glu | Gln | Leu<br>195 | Thr | Thr | Ala | Ser | Glu<br>200 | His | Cys | Asp | Leu | Ala<br>205 | Ile | Lys | Thr |
| Val | Glu<br>210 | Glu | Ile | Glu | Gly | Val<br>215 | Leu | Gly | Arg | Asp | Leu<br>220 | Tyr | Pro | Asn | Leu |
| Ala<br>225 | Glu | Glu | Arg | Ser | Arg<br>230 | Trp | Glu | Lys | Glu | Leu<br>235 | Ala | Gly | Leu | Arg | Glu<br>240 |
| Glu | Asn | Glu | Ser | Leu<br>245 | Thr | Ala | Met | Leu | Cys<br>250 | Ser | Lys | Glu | Glu | Glu<br>255 | Leu |
| Asn | Arg | Thr | Lys<br>260 | Ala | Thr | Met | Asn | Ala<br>265 | Ile | Arg | Glu | Glu | Arg<br>270 | Asp | Arg |
| Leu | Arg | Arg<br>275 | Arg | Val | Arg | Glu | Leu<br>280 | Gln | Thr | Arg | Leu | Gln<br>285 | Ser | Val | Gln |
| Ala | Thr<br>290 | Gly | Pro | Ser | Ser | Pro<br>295 | Gly | Arg | Leu | Thr | Ser<br>300 | Thr | Asn | Arg | Pro |
| Ile<br>305 | Asn | Pro | Ser | Thr | Gly<br>310 | Glu | Leu | Ser | Thr | Ser<br>315 | Ser | Ser | Ser | Asn | Asp<br>320 |
| Ile | Pro | Ile | Ala | Lys<br>325 | Ile | Ala | Glu | Arg | Val<br>330 | Lys | Leu | Ser | Lys | Thr<br>335 | Arg |
| Ser | Glu | Ser | Ser<br>340 | Ser | Ser | Asp | Arg | Pro<br>345 | Val | Leu | Gly | Ser | Glu<br>350 | Ile | Ser |
| Ser | Ile | Gly<br>355 | Val | Ser | Ser | Ser | Val<br>360 | Ala | Glu | His | Leu | Ala<br>365 | His | Ser | Leu |
| Gln | Asp<br>370 | Cys | Ser | Asn | Ile | Gln<br>375 | Glu | Ile | Phe | Gln | Thr<br>380 | Leu | Tyr | Ser | His |
| Gly<br>385 | Ser | Ala | Ile | Ser | Glu<br>390 | Ser | Lys | Ile | Arg | Glu<br>395 | Phe | Glu | Val | Glu | Thr<br>400 |

-continued

| | | | | | | | | | | | | | | |
|---|---|---|---|---|---|---|---|---|---|---|---|---|---|---|
| Glu | Arg | Leu | Asn | Ser 405 | Arg | Ile | Glu | His | Leu 410 | Lys | Ser | Gln | Asn | Asp 415 | Leu |
| Leu | Thr | Ile | Thr 420 | Leu | Glu | Glu | Cys | Lys 425 | Ser | Asn | Ala | Glu | Arg 430 | Met | Ser |
| Met | Leu | Val 435 | Gly | Lys | Tyr | Glu | Ser 440 | Asn | Ala | Thr | Ala | Leu 445 | Arg | Leu | Ala |
| Leu | Gln 450 | Tyr | Ser | Glu | Gln | Cys 455 | Ile | Glu | Ala | Tyr | Glu 460 | Leu | Leu | Leu | Ala |
| Leu 465 | Ala | Glu | Ser | Glu | Gln 470 | Ser | Leu | Ile | Leu | Gly 475 | Gln | Phe | Arg | Ala | Ala 480 |
| Gly | Val | Gly | Ser | Ser 485 | Pro | Gly | Asp | Gln | Ser 490 | Gly | Asp | Glu | Asn | Ile 495 | Thr |
| Gln | Met | Leu | Lys 500 | Arg | Ala | His | Asp | Cys 505 | Arg | Lys | Thr | Ala | Glu 510 | Asn | Ala |
| Ala | Lys | Ala 515 | Leu | Leu | Met | Lys | Leu 520 | Asp | Gly | Ser | Cys | Gly 525 | Gly | Ala | Phe |
| Ala | Val 530 | Ala | Gly | Cys | Ser | Val 535 | Gln | Pro | Trp | Glu | Ser 540 | Leu | Ser | Ser | Asn |
| Ser 545 | His | Thr | Ser | Thr | Thr 550 | Ser | Ser | Thr | Ala | Ser 555 | Ser | Cys | Asp | Thr | Glu 560 |
| Phe | Thr | Lys | Glu | Asp 565 | Glu | Gln | Arg | Leu | Lys 570 | Asp | Tyr | Ile | Gln | Gln 575 | Leu |
| Lys | Asn | Asp | Arg 580 | Ala | Ala | Val | Lys | Leu 585 | Thr | Met | Leu | Glu | Leu 590 | Glu | Ser |
| Ile | His | Ile 595 | Asp | Pro | Leu | Ser | Tyr 600 | Asp | Val | Lys | Pro | Arg 605 | Gly | Asp | Ser |
| Gln | Arg 610 | Leu | Asp | Leu | Glu | Asn 615 | Ala | Val | Leu | Met | Gln 620 | Glu | Leu | Met | Ala |
| Met 625 | Lys | Glu | Glu | Met | Ala 630 | Glu | Leu | Lys | Ala | Gln 635 | Leu | Tyr | Leu | Leu | Glu 640 |
| Lys | Glu | Lys | Lys | Ala 645 | Leu | Glu | Leu | Lys | Leu 650 | Ser | Thr | Arg | Glu | Ala 655 | Gln |
| Glu | Gln | Ala | Tyr 660 | Leu | Val | His | Ile | Glu 665 | His | Leu | Lys | Ser | Glu 670 | Val | Glu |
| Glu | Gln | Lys 675 | Glu | Gln | Arg | Met | Arg 680 | Ser | Leu | Ser | Ser | Thr 685 | Ser | Ser | Gly |
| Ser | Lys 690 | Asp | Lys | Pro | Gly | Lys 695 | Glu | Cys | Ala | Asp | Ala 700 | Ala | Ser | Pro | Ala |
| Leu 705 | Ser | Leu | Ala | Glu | Leu 710 | Arg | Thr | Thr | Cys | Ser 715 | Glu | Asn | Glu | Leu | Ala 720 |
| Ala | Glu | Phe | Thr | Asn 725 | Ala | Ile | Arg | Arg | Glu 730 | Lys | Lys | Leu | Lys | Ala 735 | Arg |
| Val | Gln | Glu | Leu 740 | Val | Ser | Ala | Leu | Glu 745 | Arg | Leu | Thr | Lys | Ser 750 | Ser | Glu |
| Ile | Arg | His 755 | Gln | Gln | Ser | Ala | Glu 760 | Phe | Val | Asn | Asp | Leu 765 | Lys | Arg | Ala |
| Asn | Ser 770 | Asn | Leu | Val | Ala | Ala 775 | Tyr | Glu | Lys | Ala | Lys 780 | Lys | Lys | His | Gln |
| Asn 785 | Lys | Leu | Lys | Lys | Leu 790 | Glu | Ser | Gln | Met | Met 795 | Ala | Met | Val | Glu | Arg 800 |
| His | Glu | Thr | Gln | Val 805 | Arg | Met | Leu | Lys | Gln 810 | Arg | Ile | Ala | Leu | Leu 815 | Glu |
| Glu | Glu | Asn | Ser | Arg 820 | Pro | His | Thr | Asn | Glu 825 | Thr | Ser | Leu | | | |

( 2 ) INFORMATION FOR SEQ ID NO:3:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( v i i i ) POSITION IN GENOME:
        ( A ) CHROMOSOME/SEGMENT: 5q21

( x i ) SEQUENCE DESCRIPTION: SEQ ID NO:3:

GAATTCATCA GCACTTCT                           18

( 2 ) INFORMATION FOR SEQ ID NO:4:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( v i i i ) POSITION IN GENOME:
        ( A ) CHROMOSOME/SEGMENT: 5q21

( x i ) SEQUENCE DESCRIPTION: SEQ ID NO:4:

CAGCTCCAAG ATGGAGGG                           18

( 2 ) INFORMATION FOR SEQ ID NO:5:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( v i i i ) POSITION IN GENOME:
        ( A ) CHROMOSOME/SEGMENT: 5q21

( x i ) SEQUENCE DESCRIPTION: SEQ ID NO:5:

GGCCCCATGT GCTTTGTT                           18

( 2 ) INFORMATION FOR SEQ ID NO:6:

( i ) SEQUENCE CHARACTERISTICS:

```
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens (viii) POSITION IN GENOME:
         (A) CHROMOSOME/SEGMENT: 5q21

(xi) SEQUENCE DESCRIPTION: SEQ ID NO:6:

AGAGGGACTC TGGAGACA                                                    18

(2) INFORMATION FOR SEQ ID NO:7:

(i) SEQUENCE CHARACTERISTICS:
         (A) LENGTH: 20 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens (viii) POSITION IN GENOME:
         (A) CHROMOSOME/SEGMENT: 5q21

(xi) SEQUENCE DESCRIPTION: SEQ ID NO:7:

ATGTTGATTA ATCCGTTGGC                                                  20

(2) INFORMATION FOR SEQ ID NO:8:

(i) SEQUENCE CHARACTERISTICS:
         (A) LENGTH: 18 base pairs
         (B) TYPE: nucleic acid
         (C) STRANDEDNESS: single
         (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Homo sapiens (viii) POSITION IN GENOME:
         (A) CHROMOSOME/SEGMENT: 5q21

(xi) SEQUENCE DESCRIPTION: SEQ ID NO:8:

ACCCCAGAGC AGAAGGCT                                                    18

(2) INFORMATION FOR SEQ ID NO:9:

(i) SEQUENCE CHARACTERISTICS:
         (A) LENGTH: 18 base pairs
         (B) TYPE: nucleic acid
         (C) STRANDEDNESS: single
         (D) TOPOLOGY: linear
```

( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: Homo sapiens ( v i i i ) POSITION IN GENOME:
            ( A ) CHROMOSOME/SEGMENT: 5q21

( x i ) SEQUENCE DESCRIPTION: SEQ ID NO:9:

GGCCTAACTG GAATGTGT                                                                 18

( 2 ) INFORMATION FOR SEQ ID NO:10:

( i ) SEQUENCE CHARACTERISTICS:
            ( A ) LENGTH: 18 base pairs
            ( B ) TYPE: nucleic acid
            ( C ) STRANDEDNESS: single
            ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
            ( A ) ORGANISM: Homo sapiens ( v i i i ) POSITION IN GENOME:
            ( A ) CHROMOSOME/SEGMENT: 5q21

( x i ) SEQUENCE DESCRIPTION: SEQ ID NO:10:

GCCCAGATAA ACACCAGC                                                                 18

( 2 ) INFORMATION FOR SEQ ID NO:11:

( i ) SEQUENCE CHARACTERISTICS:
            ( A ) LENGTH: 24 amino acids
            ( B ) TYPE: amino acid
            ( C ) STRANDEDNESS: single
            ( D ) TOPOLOGY: linear ( i i ) MOLECULE TYPE: peptide ( i i i ) HYPOTHETICAL: NO ( i v ) ANTI-SENSE: NO ( v ) FRAGMENT TYPE: internal ( v i ) ORIGINAL SOURCE:
            ( A ) ORGANISM: Homo sapiens ( x i ) SEQUENCE DESCRIPTION: SEQ ID NO:11:

Leu  Tyr  Trp  Arg  Ile  Tyr  Lys  Glu  Thr  Glu  Lys  Arg  Thr  Lys  Glu  Leu
    1                   5                        10                       15

Ala  Gly  Leu  Gln  Ala  Ser  Gly  Thr
                   20

( 2 ) INFORMATION FOR SEQ ID NO:12:

( i ) SEQUENCE CHARACTERISTICS:
            ( A ) LENGTH: 206 base pairs
            ( B ) TYPE: nucleic acid
            ( C ) STRANDEDNESS: double
            ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
(A) ORGANISM: Homo sapiens ( i x ) FEATURE:
(A) NAME/KEY: CDS
(B) LOCATION: 32..172

( i x ) FEATURE:
(A) NAME/KEY: exon
(B) LOCATION: 32..174

( x i ) SEQUENCE DESCRIPTION: SEQ ID NO:12:

```
CAGCACTTCT GTCCTTTTCC CTTATTCCCA G TGC GAG CAG TCC CAC CTC ATG            52
                                   Cys Glu Gln Ser His Leu Met
                                    1               5

AGA GAG CAT GAG GAT GTC CAG GAG CGA ACG ACG CTT CGC TAT GAG GAA          100
Arg Glu His Glu Asp Val Gln Glu Arg Thr Thr Leu Arg Tyr Glu Glu
         10              15                  20

CGC ATC ACA GAG CTC CAC AGC GTC ATT GCG GAG CTC AAC AAG AAG ATA         148
Arg Ile Thr Glu Leu His Ser Val Ile Ala Glu Leu Asn Lys Lys Ile
     25              30                  35

GAC CGT CTG CAA GGC ACC ACC ATC AGGTACGCGG CTCCATTCGG CTTTTACTCT         202
Asp Arg Leu Gln Gly Thr Thr Ile
 40              45

GCCC                                                                     206
```

( 2 ) INFORMATION FOR SEQ ID NO:13:

( i ) SEQUENCE CHARACTERISTICS:
(A) LENGTH: 47 amino acids
(B) TYPE: amino acid
(D) TOPOLOGY: linear ( i i ) MOLECULE TYPE: protein ( x i ) SEQUENCE DESCRIPTION: SEQ ID NO:13:

```
Cys Glu Gln Ser His Leu Met Arg Glu His Glu Asp Val Gln Glu Arg
 1               5                  10                  15

Thr Thr Leu Arg Tyr Glu Glu Arg Ile Thr Glu Leu His Ser Val Ile
             20                  25                  30

Ala Glu Leu Asn Lys Lys Ile Asp Arg Leu Gln Gly Thr Thr Ile
         35                  40                  45
```

( 2 ) INFORMATION FOR SEQ ID NO:14:

( i ) SEQUENCE CHARACTERISTICS:
(A) LENGTH: 206 base pairs
(B) TYPE: nucleic acid
(C) STRANDEDNESS: double
(D) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
(A) ORGANISM: Rattus rattus ( i x ) FEATURE:
(A) NAME/KEY: exon
(B) LOCATION: 32..174

( i x ) FEATURE:
(A) NAME/KEY: CDS ( B ) LOCATION: 32..172

( x i ) SEQUENCE DESCRIPTION: SEQ ID NO:14:

```
TCCGTCTTCT CCTCTTTGTT CTTGGCCCTA G TGT GAG CAG TCA CAC CTC ATG        52
                                  Cys Glu Gln Ser His Leu Met
                                   1               5

AGA GAG CAT GAA GAT GTT CAG GAA CGC ACG ACA CTC CGC TAT GAG GAG       100
Arg Glu His Glu Asp Val Gln Glu Arg Thr Thr Leu Arg Tyr Glu Glu
         10              15                  20

CGC ATC ACA GAG CTC CAC AGC ATC ATT GCA GAA CTC AAC AAG AAG ATA       148
Arg Ile Thr Glu Leu His Ser Ile Ile Ala Glu Leu Asn Lys Lys Ile
         25              30                  35

GAC CGC TTG CAA GGT ACC ACC ATC AGGTATGGCT GCTATTAAC CTGTGCTGGT       202
Asp Arg Leu Gln Gly Thr Thr Ile
40              45

CCTT                                                                  206
```

( 2 ) INFORMATION FOR SEQ ID NO:15:

( i ) SEQUENCE CHARACTERISTICS:
        ( A ) LENGTH: 47 amino acids
        ( B ) TYPE: amino acid
        ( D ) TOPOLOGY: linear ( i i ) MOLECULE TYPE: protein ( x i ) SEQUENCE DESCRIPTION: SEQ ID NO:15:

```
Cys Glu Gln Ser His Leu Met Arg Glu His Glu Asp Val Gln Glu Arg
 1               5                  10                  15

Thr Thr Leu Arg Tyr Glu Glu Arg Ile Thr Glu Leu His Ser Ile Ile
             20                  25                  30

Ala Glu Leu Asn Lys Lys Ile Asp Arg Leu Gln Gly Thr Thr Ile
             35                  40                  45
```

( 2 ) INFORMATION FOR SEQ ID NO:16:

( i ) SEQUENCE CHARACTERISTICS:
        ( A ) LENGTH: 208 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Homo sapiens ( v i i i ) POSITION IN GENOME:
        ( A ) CHROMOSOME/SEGMENT: 5q21

( i x ) FEATURE:
        ( A ) NAME/KEY: CDS
        ( B ) LOCATION: 35..175

( i x ) FEATURE:
        ( A ) NAME/KEY: exon
        ( B ) LOCATION: 34..176

( x i ) SEQUENCE DESCRIPTION: SEQ ID NO:16:

```
TGTTAGTGGT TGCCAATTCT CCTTTTTCT CAGG GAG GAA GAT GAG TAC TCA          52
                                    Glu Glu Asp Glu Tyr Ser
                                     1               5

GAA CTG CGA TCA GAA CTC AGC CAG AGC CAA CAC GAG GTC AAC GAG GAC       100
Glu Leu Arg Ser Glu Leu Ser Gln Ser Gln His Glu Val Asn Glu Asp
```

```
                         10                         15                         20
TCT CGA AGC ATG GAC CAA GAC CAG ACC TCT GTC TCT ATC CCC GAA AAC              148
Ser Arg Ser Met Asp Gln Asp Gln Thr Ser Val Ser Ile Pro Glu Asn
        25                          30                      35

CAG TCT ACC ATG GTT ACT GCT GAC ATG GGTGAGTCTG CCTGCCCTTG                    195
Gln Ser Thr Met Val Thr Ala Asp Met
    40                      45

CCACCAAGCC AGA                                                                208
```

( 2 ) INFORMATION FOR SEQ ID NO:17:

( i ) SEQUENCE CHARACTERISTICS:
        ( A ) LENGTH: 47 amino acids
        ( B ) TYPE: amino acid
        ( D ) TOPOLOGY: linear ( i i ) MOLECULE TYPE: protein ( x i ) SEQUENCE DESCRIPTION: SEQ ID NO:17:

```
Glu Glu Asp Glu Tyr Ser Glu Leu Arg Ser Glu Leu Ser Gln Ser Gln
 1               5                  10                  15

His Glu Val Asn Glu Asp Ser Arg Ser Met Asp Gln Asp Gln Thr Ser
            20                  25                  30

Val Ser Ile Pro Glu Asn Gln Ser Thr Met Val Thr Ala Asp Met
        35                  40                  45
```

( 2 ) INFORMATION FOR SEQ ID NO:18:

( i ) SEQUENCE CHARACTERISTICS:
        ( A ) LENGTH: 208 base pairs
        ( B ) TYPE: nucleic acid
        ( C ) STRANDEDNESS: double
        ( D ) TOPOLOGY: linear ( i i ) MOLECULE TYPE: DNA (genomic)

( i i i ) HYPOTHETICAL: NO ( i v ) ANTI-SENSE: NO ( v i ) ORIGINAL SOURCE:
        ( A ) ORGANISM: Rattus rattus ( i x ) FEATURE:
        ( A ) NAME/KEY: exon
        ( B ) LOCATION: 34..176

( i x ) FEATURE:
        ( A ) NAME/KEY: CDS
        ( B ) LOCATION: 35..175

( x i ) SEQUENCE DESCRIPTION: SEQ ID NO:18:

```
CACTCAATGG TGAGTGGCTC TCTTTTTTTG CAGG GAG GAA GAT GAG TAC TCA                 52
                                     Glu Glu Asp Glu Tyr Ser
                                      1               5

GAA CTT CGG TCA GAG CTC AGC CAG AGT CAA CAA GAG GTC AAT GAA GAC              100
Glu Leu Arg Ser Glu Leu Ser Gln Ser Gln Gln Glu Val Asn Glu Asp
            10                  15                      20

TCC AGA AGT GTG GAC CAA GAC CAG ACC TCT GTG TCC ATC CCT GAG AAC              148
Ser Arg Ser Val Asp Gln Asp Gln Thr Ser Val Ser Ile Pro Glu Asn
        25                      30                  35

CAG TCT ACT ATG GTC ACT GCT GAC ATG GGTGAGTCTT CCCAGGCCTC                    195
Gln Ser Thr Met Val Thr Ala Asp Met
    40                      45

CTGCTTAGTT TCT                                                                208
```

( 2 ) INFORMATION FOR SEQ ID NO:19:

( i ) SEQUENCE CHARACTERISTICS:
        ( A ) LENGTH: 47 amino acids
        ( B ) TYPE: amino acid
        ( D ) TOPOLOGY: linear ( i i ) MOLECULE TYPE: protein ( x i ) SEQUENCE DESCRIPTION: SEQ ID NO:19:

```
Glu Glu Asp Glu Tyr Ser Glu Leu Arg Ser Glu Leu Ser Gln Ser Gln
 1               5                  10                  15

Gln Glu Val Asn Glu Asp Ser Arg Ser Val Asp Gln Asp Gln Thr Ser
            20                  25                  30

Val Ser Ile Pro Glu Asn Gln Ser Thr Met Val Thr Ala Asp Met
            35                  40                  45
```